(12) United States Patent
Rosse

(10) Patent No.: US 6,640,212 B1
(45) Date of Patent: Oct. 28, 2003

(54) STANDARDIZED INFORMATION MANAGEMENT SYSTEM FOR LONG-TERM RESIDENCE FACILITIES

(76) Inventor: Rodney L. Rosse, 8156 Xenia Ave. N., Brooklyn Park, MN (US) 55443-2330

( * ) Notice: Subject to any disclaimer, the term of this patent is extended or adjusted under 35 U.S.C. 154(b) by 0 days.

(21) Appl. No.: 09/409,979

(22) Filed: Sep. 30, 1999

(51) Int. Cl.[7] .............................................. G06F 17/60
(52) U.S. Cl. ................... 705/9; 705/8; 705/2; 600/595
(58) Field of Search ...................... 705/9, 8, 2; 600/595

(56) References Cited

U.S. PATENT DOCUMENTS

| | | | | |
|---|---|---|---|---|
| 4,803,625 A | | 2/1989 | Fu et al. ..................... 600/483 |
| 4,857,716 A | * | 8/1989 | Gombrich et al. .......... 235/375 |
| 5,065,315 A | * | 11/1991 | Garcia .......................... 705/2 |
| 5,199,439 A | | 4/1993 | Zimmerman et al. ....... 600/483 |
| 5,307,263 A | | 4/1994 | Brown ........................ 600/301 |
| 5,542,420 A | | 8/1996 | Goldman et al. ........... 600/301 |
| 5,558,638 A | | 9/1996 | Evers et al. ................... 604/66 |
| 5,583,758 A | * | 12/1996 | McIlroy et al. ................ 705/2 |
| 5,691,932 A | | 11/1997 | Reiner et al. ................ 368/10 |
| 5,692,215 A | | 11/1997 | Kutzik et al. ................ 710/18 |
| 5,732,401 A | | 3/1998 | Conway ...................... 705/29 |
| 5,732,709 A | | 3/1998 | Tacklind et al. ............ 600/539 |
| 5,748,907 A | * | 5/1998 | Crane ............................ 705/2 |
| 5,799,286 A | | 8/1998 | Morgan et al. .............. 705/30 |
| 5,810,747 A | * | 9/1998 | Brudny et al. .............. 600/595 |
| 5,845,253 A | | 12/1998 | Rensimer ...................... 705/2 |
| 5,890,997 A | | 4/1999 | Roth ............................. 482/8 |
| 5,995,937 A | * | 11/1999 | DeBusk et al. ................ 705/2 |
| 6,139,494 A | * | 10/2000 | Cairnes ...................... 600/300 |
| 6,201,948 B1 | * | 3/2001 | Cook et al. ................. 434/350 |
| 6,308,164 B1 | * | 10/2001 | Nummelin et al. ........... 705/9 |
| 6,401,072 B1 | * | 6/2002 | Haudenschild et al. ........ 705/3 |

FOREIGN PATENT DOCUMENTS

WO WO 00/72181 * 11/2000

OTHER PUBLICATIONS

Phillips, R.M., and Baldwin, B.A., Teaching Psychosocial Care to Long–Term Nursing Assistants, May/Jun. 1997, The Journal of Continuing Education in Nursing, vol. 28, pp. 130–134.*

U.S. patent application Ser. No. 09/210,951, Baughman et al., filed Dec. 15, 1998.

* cited by examiner

Primary Examiner—Tariq R. Hafiz
Assistant Examiner—Andre Boyce
(74) Attorney, Agent, or Firm—Patterson, Thuente, Skaar & Christensen, P.A.

(57) ABSTRACT

A standardized information management system for use in long-term residence facilities continually collects and manages all direct-care information related to both the clients and staff of the facility. The collection and management of this information is standardized to create consistency, stability, and improvement in the care, tracking and teaching of the clients of the facility. To facilitate this standardization, the information management system breaks activities and duties down into a set of defined duties, each of which represent a unit of assignable work that involves a client, a staff member or both. The step-by-step tasks that comprise a given duty are individually definable using a standardized database process. Duties may be clustered together to form activities. Activities are scheduled on a daily basis based on staff availability and qualifications and appropriateness to client needs and preferences. A comprehensive plan for each client is created by the daily schedule of activities. The plan is displayed for staff members by the system and the performance of each activity is recorded in the system using standardized rating scales and special data set-ups as appropriate. The system also allows for recording of periodic information on health and behavior management issues. All of this information is compiled by the system for analysis to generate standardized and customized reports.

22 Claims, 32 Drawing Sheets

Fig. 3

FOOD/FLUIDS/TOILETING SUMMARIES:

For Period of 9/2/99 thru 9/15/99

REGULAR MEALS

| A.M. MEALS | MIDDAY MEALS | EVENING MEALS |
|---|---|---|

Legend:
- Little or Nothing
- Ate Less than 1/2
- Ate More than 1/2
- Ate Whole Meal

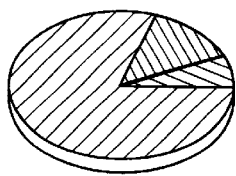 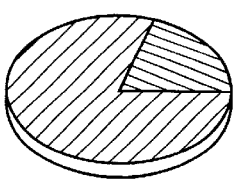 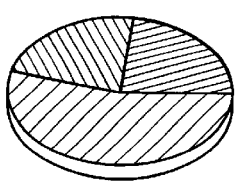

15 Meals (Before Noon or After 11p)   5 Meals (12p - 5p)   13 Meals (5p - 11p)

Average Daily Count (by hour) of Snacks by Type of Food

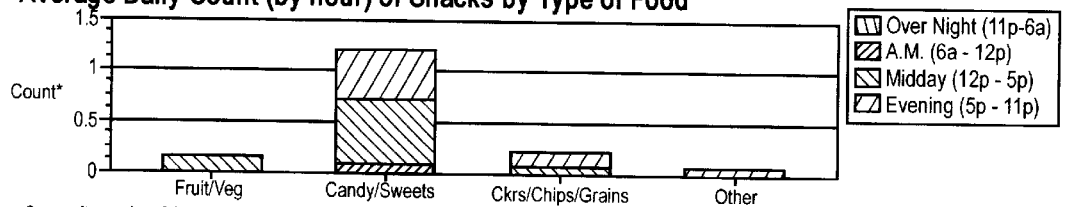

Legend:
- Over Night (11p-6a)
- A.M. (6a - 12p)
- Midday (12p - 5p)
- Evening (5p - 11p)

*ea. unit consist of 1 hour during which the indicated food was consumed.

Average Daily Intake of Fluids by Type of Beverage

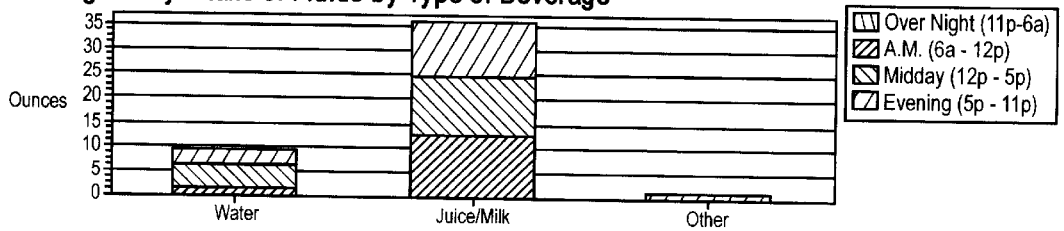

Legend:
- Over Night (11p-6a)
- A.M. (6a - 12p)
- Midday (12p - 5p)
- Evening (5p - 11p)

Average Daily Instances of Toileting

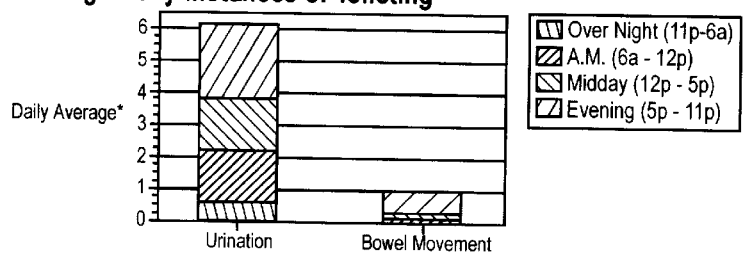

Legend:
- Over Night (11p-6a)
- A.M. (6a - 12p)
- Midday (12p - 5p)
- Evening (5p - 11p)

*ea. unit represents an hour during which the instance was recorded.

Fig. 4

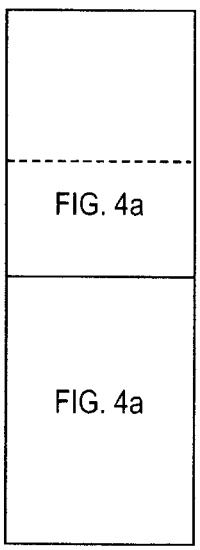

Fig. 4a

Personal Interaction Independence and Integration (PIII) Programs Implemented
During Month of 08/01/1999 thru 08/31/1999
for XXX Category 2./1 PIII: Personal Choice and Initiative
  #555. Make Pudding (Recommended Frequency: Once/month)
    08/31
    Total Number of Days = 1; Number of Times Program Run = 1
Category 2./1 PIII: Personal Choice and Initiative
  #558. Make Popcorn (Recommended Frequency: Twice/month)
    08/05, 08/19
    Total Number of Days = 2; Number of Times Program Run = 2
Category 2./1 PIII: Personal Choice and Initiative
  #559. Errands (Recommended Frequency: Four Times/week)
    08/01, 08/03, 08/07, 08/08, 08/10, 08/12, 08/14, 08/15, 08/17, 08/17, 08/19, 08/20, 08/21,
    08/24, 08/26, 08/28, 08/29, 08/31
    Total Number of Days = 17; Number of Times Program Run = 17
Category 2./1 PIII: Personal Choice and Initiative
  #560. Make Juice (Recommended Frequency: Twice/month)
    08/06, 08/07
    Total Number of Days = 2; Number of Times Program Run = 2
Category 2./1 PIII: Personal Choice and Initiative
  #561. Arts and Crafts (Recommended Frequency: Twice/month)
    08/01, 08/08, 08/14, 08/15, 08/22
    Total Number of Days = 5; Number of Times Program Run = 5

Category 2./1 PIII: Personal Choice and Initiative
   #1417. Puzzles (Recommended Frequency: Once/day)
      08/01, 08/03, 08/04, 08/05, 08/06(2), 08/07, 08/08, 08/09, 08/11, 08/12, 08/13, 08/14, 08/15,
      08/17, 08/18, 08/19(2), 08/20(2), 08/21, 08/22, 08/23, 08/25, 08/27, 08/28, 08/29, 08/30, 08/31
      Total Number of Days = 28; Number of Times Program Run = 31
Category 2./1 PIII: Personal Choice and Initiative
   #1416. Legos (Recommended Frequency: Twice/day)
      08/01, 08/02(2), 08/02(2), 08/04(2), 08/06, 08/07(2), 08/08(2), 08/09(2), 08/10(2), 08/11(2),
      08/12, 08/13, 08/14(2), 08/15(2), 08/16, 08/17(3), 08/18(2), 08/19(3), 08/20(4), 08/21(3),
      08/22, 08/23, 08/24(2), 08/25(2), 08/26, 08/27, 08/28, 08/29(2), 08/30, 08/31(2)
      Total Number of Days = 30; Number of Times Program Run = 55
Category 2./1 PIII: Personal Choice and Initiative
   #2113. Restaurant with Peer (Recommended Frequency: One Time/week)
      08/06, 08/020
      Total Number of Days = 2; Number of Times Program Run = 2
Category 2./1 PIII: Personal Choice and Initiative
   #564. Visit Apartments (Recommended Frequency: Two Times/week)
      08/06, 08/05, 08/19
      Total Number of Days = 3; Number of Times Program Run = 3
Category 2./1 PIII: Personal Choice and Initiative
   #565. Shake Hands (Recommended Frequency: Three Times/week)
      08/01, 08/04, 08/06, 08/08, 08/11, 08/13, 08/15, 08/18, 08/20, 08/22, 08/25, 08/27, 08/29
      Total Number of Days = 13; Number of Times Program Run = 13
Category 2./1 PIII: Personal Choice and Initiative
   #567. Peer Activity (Recommended Frequency: Four Times/week)
      08/01, 08/02, 08/03, 08/06, 08/07(2), 08/08, 08/10, 08/12, 08/14, 08/19, 08/22, 08/24, 08/26,
      08/27, 08/29

Assessment of (name of client)
Prepared for (name of person/agency)
Dated covered: July 21, 1996 - Aug 27, 1999

Office Document: Aug. 27, 1999; 2:35 pm

Performance by Service Category:

|  |  | HISTORICAL Admission to July 27, 1998 | | PREVIOUS YEAR July 27, 1998 July 27, 1999 | | PREVIOUS MONTH July 27, 1999 Aug. 27, 1999 | |
|---|---|---|---|---|---|---|---|
|  |  | No. Tasks | Perf. | No. Tasks | Perf. | No. Tasks | Perf. |
| 2.0 Personal Interaction, Indep., and Integ. (PIII) | | | | | | | |
| 2.1 Personal Choice Initiative | Carry Over | 0 | 0 | 236 | 4.1 | 287 | 4.2 |
|  | New Tasks | 236 | 3.8 | 51 | 3.6 | 18 | 2.7 |
|  | Total Tasks | 236 | 3.8 | 287 | 4.0 | 305 | 4.1 |
| 2.2 Development of Social Interaction | Carry Over | | | | | | |
|  | New Tasks | | | ...ditto... | | | |
|  | Total Tasks | | | | | | |

...etc 4.0 Activities of Daily Living (ADL)
4.1 Dressing
4.2 Grooming
...etc.

Performance by Skill:

|  |  | HISTORICAL | | PREVIOUS YEAR | | PREVIOUS MONTH | |
|---|---|---|---|---|---|---|---|
|  |  | No. Tasks | Perf. | No. Tasks | Perf. | No. Tasks | Perf. |
| I. Motor Skills | | | | | | | |
| A Fine Motor | Carry Over | 0 | 0 | 236 | 4.1 | 287 | 4.2 |
|  | New Tasks | 236 | 3.8 | 51 | 3.6 | 18 | 2.7 |
|  | Total Tasks | 236 | 3.8 | 287 | 4.0 | 305 | 4.1 |
| B. Gross Motor | | | | | | | |
| C. Positioning | | | | ...ditto... | | | |
| ... etc. | | | | | | | |
| II. Communication | | | | | | | |
| A. Expressive | | | | ...ditto... | | | |
| B. Recpetive | | | | | | | |
| ... etc. | | | | | | | |
| III. ... etc. | | | | | | | |

Frequency of Staff Duty Implementation by Category:

|  |  | HISTORICAL | | PREVIOUS YEAR | | PREVIOUS MONTH | |
|---|---|---|---|---|---|---|---|
|  |  | No. | Freq/wk | No. | Freq/wk | No. | Freq/wk |
| 2.0 Personal Interaction, Indep., and Integ. (PIII) | | | | | | | |
| 2.1 Personal Choice and Initiative | Carry Over | 0 | 0 | 96 | 402 | 112 | 476 |
|  | New Duties | 96 | 460 | 21 | 91 | 6 | 21 |
|  | Total Duties | 96 | 460 | 117 | 493 | 118 | 496 |
| 2.2 Developmental of Social Interaction | Carry Over | | | | | | |
|  | New Duties | | | ...ditto... | | | |
|  | Total Duties | | | | | | |
| 2.3 ... etc. | | | | | | | |

4.0 Activities of Daily Living (ADL)
4.1 Dressing       ...ditto...
4.2 Grooming
4.3  ... etc.

Vehicle Scheduling:

Vehicle Schedule for Sunday, September 19, 1999

| Ford | Dodge |
|---|---|

| Time | Type | Dept | Purpose |
|---|---|---|---|
| 5:30p - 9:30p | Routine | CRS | Supplementary Leisure |

Schedule New Entry for Ford — Auto Close / Delete Entry

● One-Time-Only
○ Weekly

Department: South  From: 3:30p  To: 4:30p

Purpose: Medical Appointment

✗ Cancel   ✓ OK

⇐ Back One Day    Finished    Forward One Day ⇒

Fig. 9

Planning and Organizing Duties:
Client:     Kiosk: South

Planned Activities | Supporting Services

- Breakfast
  - Prepare Breakfast
  - Prepare Cereal
  - Use Toaster
  - Pour Beverage
  - Clean Place Setting
- Morning Dressing/Grooming
  - Dress Weather Appropriate
  - Brush Teeth
  - Brush/Comb Hair
  - Apply Deodorant
  - Apply Lotion
  - Clip Nails
  - File Nails
  - Use Toilet
- Engaging in Hobbies
  - Listen to Records
  - Take Pictures
  - Call Family Members
  - Write in Room
  - Write To Friends and Family
  - Write in Journal
  - Bake Muffins
  - Watch Video
- Cleaning
  - Clean Kitchen
  - Wipe Tables
  - Take Out Trash
  - Sweep Floor Duties Indexed by Category

- 2.0 Personal Interaction, Independence, and Integration (
  - 2.1 PIII: Personal Choice and Initiative
  - 2.2 PIII: Development of Social Interaction
  - 2.3 PIII: Development of Personal Responsibility
  - 2.4 PIII: Community Leisure Experience
  - 2.5 PIII: Community Integration
  - 2.6 PIII: Community Skills Acquisition
- 3.0 Challenging Behavior and Preventive Practices (CBP
  - 3.1 CBPP: Self Injurious Behavior
  - 3.2 CBPP: Unusual or Repetitive Habits
  - 3.3 CBPP: Withdrawal Behavior
  - 3.4 CBPP: Hurtful to Others
  - 3.5 CBPP: Socially Offensive Behavior
  - 3.6 CBPP: Destruction of Property
  - 3.7 CBPP: Wandering
  - 3.8 CBPP: Susceptibility to Victimization
- 4.0 Activities of Daily Living (ADL)
  - 4.1 ADL: Dressing
  - 4.2 ADL: Grooming
  - 4.3 ADL: Bathing
  - 4.4 ADL: Eating
  - 4.5 ADL: Transfer
  - 4.6 ADL: Mobility
  - 4.7 ADL: Toileting
  - 4.8 ADL: Self Preservation
- 5.0 Medical/Dental Health
  - 5.1 Medical/Dental Appointment
  - 5.2 Special Procedures
  - 5.3 Pass Medication
- 6.0 Documentation (Alphabetic Order Maintained within Category)

✓ Save & Quit

Fig. 10

Planning and Organizing Duties:
Client:  Kiosk: South

Planned Activities | Supporting Services

- Challenging Behaviors
  - Self Injurious Behavior
    - Monitor fo— | Delete
    - Unusual or Re | Edit Node
    - Monitor fo | New Node
    - Monitor F | New Sub-Node
    - Monitor F | Assign Duty under Self Injurious Behavior
    - Withdrawal Be | Copy
    - Monitor Fo | Cut
    - Hurtful to Othe | Paste
    - Monitor For ~~Dumping Smit~~
  - Socially Offensive Behavior
    - Monitor For Inapprop Urination
    - Monitor For Inappropriate BM
    - Monitor For Loud Voice
  - Destruction of Property
  - Wandering
    - Monitor For Wandering
  - Susceptibility to Victimization
- Medical
- Financial
  - Balance Money
- Domestic
- Personal
  - Chart HPNs
  - Prompt To Ask Permission
  - Community Duties Indexed by Category
- ◇ 2.0 Personal Interaction, Independence, and Integration (PII)
- ◇ 3.0 Challenging Behavior and Preventive Practices (CBPP)
- ◇ 4.0 Activities of Daily Living (ADL)
- ◇ 5.0 Medical/Dental/Health
- ◇ 6.0 Documentation
- ◇ 7.0 Personal Services (Alphabetic Order Maintained within Category)

✓ Save & Quit

Fig. 11

Planning and Organizing Duties:
Client: Kiosk, South
Assignable Direct-Care Duty Setup:

Duty #509
Client:
Posting Target: South
Duty Name: Prepare Cereal
Category: 2.3 PIII: Development of Personal Responsibility Textual Components: ✎ Supplementary Text Entry/Editing Update History:
| Date | Person | Purpose |
| 05/17/1999 | | New duty |

Priority Assignment: 3. High priority - Keep trying through out shift until completed.
Scheduling Class: Routine Scheduling;
Scheduling Options: FREQUENCY: Twice/Week
DAYS: Tues, Thurs,
TIME(s) OF DAY: Morning, Time Allotments: Resident: 5 ▶ Minutes    Staff: 5 ▶ Minutes Staff Qualifications: Special Training;

Create/Edit Task List    Assign TaskResponsibilities    * Assign Prompting Detail Special Data Print Duty Record ☑ Require Re-Training ☑ Active Duty ✓ Quit/Save Duty Task List:
- Before preparing breakfast, open cupboard containing cereal.
- When the breakfast menu includes cereal, give the cue "Time to make cereal."
- • When given the cue, choose a box of cereal from the cupboard.
- When cereal has been chosen, give the cue "Get a bowl and spoon."
- • When given cue, take out bowl and spoon.
- When bowl and spoon are on counter, give the cue "Open the box."
- • When bowl and spoon are on counter, open cereal box until both box and plastic bag are open and ready to pour.
- When box is open, pour cereal into bowl until bowl is full.
- When cereal is in bowl, take bowl to place setting.
- After cereal is prepared, say "Thanks for making cereal."
- After cereal is prepared, close the box.

Fig. 12

Client:
Duty: #509: Prepare Cereal

Before preparing breakfast, open cupboard containing cere
When the breakfast menu includes cereal, give the cue "Ti
I When given the cue, choose a box of cereal from the cup
When cereal has been chosen, give the cue "Get a bowl a
I When given cue, take out bowl and spoon.
When bowl and spoon are on counter, give the cue "Open       pen and ready to pour.
I When bowl and spoon are on counter, open cereal box u
When box is open, pour cereal into bowl until bowl is full.
When cereal is in bowl, take bowl to place setting.
After cereal is prepared, say "Thanks for making cereal."
After cereal is prepared, close the box.

| Delete |
| Cut |
| Copy |
| Paste (Insert) |
| Paste (Into a Subtask) |
| Insert Next Task |
| Add SubTask |
| Edit Task |

Outline the duty by creating statements specifying each "task" or action that needs to be taken for duty completion. Some Steps may have "sub-steps."
Each statement should/may include the following:
  Condition (required)- a statement describing the discriminative stimulus or conditions under which the action is to occur (ie. When the floor is dirty).
  Tool (optional)- may use if special tools are (ie. using broom).
  Action Phrase (required)- description of the action which is to occur (ie. sweep).
  Object Phrase (required)- description of the object which is to be acted upon (ie. kitchen floor).
  Criterion (optional)- brief statement of what needs to be accomplished before moving on (ie. until clean).
Tasks should be arranged in logical order. To move a task, click down on it and hold while moving to desired position. Tasks can only be rearranged
within level. Use the Right-Click button on see task editing options.

Task Pool Searching Options:

| Select By Client | Search by Duty Name | Search by Task Phrases |

✘ Cancel                                    ✓ OK (Save List)

Fig. 13

Client: | Duty: #509: Prepare Cereal | Listing of Previously Defined Conditions

Before preparing breakfast, open cupboard containing cereal.
When the breakfast menu includes cereal, give the cue "Time to make cereal."
When given the cue, choose a box of cereal from the cupboard.
When cereal has been chosen, give the cue "Get a bowl and spoon."
When given cue, take out bowl and spoon.
When bowl and spoon are on counter, give the cue "Open the box."
When bowl and spoon are on counter, open cereal box until both box and
When box is open, pour cereal into bowl until bowl is full.
When cereal is in bowl, take bowl to place setting.
After cereal is prepared, say "Thanks for making cereal."
After cereal is prepared, close the box.

When possible, use previously defined word or phrase by clicking on desired item below:

box is open

✗ Cancel

📁 Store New Task in Task List

Task Creation Dialog:

Condition: [When ▸] [box is open] (Required)

Tool: [using ▸] [ ] (Optional)

Action (Verb Phrase): [pour] (Required)

Object (Noun Phrase): [cereal into bowl] (Required)

Criterion: [until ▸] [bowl is full] (Optional)

Program Training Records: GES ▶  Client: DLC ▶  🔍 Add Instructor

First, Select Supervisor →

| | AOB | CMO | EAA | ESH | TDV | JAP | JEA | JLB | JLG | JLL | LSA | PDS | SRM | XJN | ALP | EEH |
|---|---|---|---|---|---|---|---|---|---|---|---|---|---|---|---|---|
| | | 5/17 | 5/17 | | 5/17 | 5/17 | 5/17 | 5/17 | 4/29 | | | | | 6/6 | 5/17 | 5/17 |
| Brush Teeth (#339) | 8/9 | 6/6 | 6/6 | 8/9 | 6/6 | 6/6 | 6/6 | 6/6 | 6/6 | | | | | 6/6 | 6/6 | 6/6 |
| Chose Aerobic Activity (#391) | 8/9 | 6/6 | 6/6 | 8/9 | 6/6 | 6/6 | 6/6 | 6/6 | 6/6 | | | | | 6/6 | 6/6 | 6/6 |
| Clean Bathroom (#406) | 8/9 | 6/6 | 6/6 | 8/9 | 6/6 | 6/6 | 6/6 | 6/6 | 6/6 | | | | | 6/6 | 6/6 | 6/6 |
| Clean Closet (#415) | 8/9 | 6/6 | | 8/9 | 6/6 | 6/6 | 6/6 | 6/6 | 6/6 | | | | | 6/6 | 6/6 | 6/6 |
| Clean Fridge (#409) | 8/9 | 6/6 | 6/6 | 8/9 | 6/6 | 6/6 | 6/6 | 6/6 | 6/6 | | | | | 6/6 | 6/6 | 6/6 |
| Clean Grooming kit (#407) | 8/9 | 6/6 | 6/6 | 8/9 | 6/6 | 6/6 | 6/6 | 6/6 | 6/6 | | | | | 6/6 | 6/6 | 6/6 |
| Clean Room (#399) | 8/9 | 6/6 | 6/6 | 8/9 | 6/6 | 6/6 | 6/6 | 6/6 | 6/6 | | | | | 6/6 | 6/6 | 6/6 |
| Clean Room in AM (#337) | 8/9 | 6/19 | | 8/9 | | 8/9 | 8/9 | 8/9 | 8/9 | 8/9 | | | | 8/6 | | 8/9 |
| Deposit Check (#432) | 8/9 | 6/6 | 6/6 | 8/9 | 6/6 | 6/6 | 6/6 | 6/6 | 6/6 | | | | | 6/6 | | 6/6 |
| Eat Meal (#336) | 8/9 | 6/6 | 6/6 | 8/9 | 6/6 | 6/6 | 6/6 | 6/6 | 6/6 | | | | | 6/6 | | 6/6 |
| Eat Snack (#412) | 8/9 | 5/31 | 6/6 | 8/9 | 6/6 | 6/6 | 6/6 | 6/6 | 6/6 | | | | | 5/31 | 6/6 | 6/6 |
| Eat at Restaurant (#375) | 8/9 | 6/6 | 6/6 | 8/9 | 6/6 | 6/6 | 6/6 | 6/6 | 6/6 | | | | | 5/31 | 6/6 | 6/6 |
| Engage in Social Sport (#387) | 8/9 | | 6/6 | 8/9 | | 8/9 | 8/9 | 8/9 | 8/9 | | | | | 8/30 | | |
| Enter Door Code (#766) | 8/9 | | | | | | | | | | | | | 8/6 | | |
| Follow Eating Rules (#414) | | 6/6 | 6/6 | 8/9 | 6/6 | 6/6 | 6/6 | 6/6 | 6/6 | | | | | 5/31 | 6/6 | 6/6 |
| Gel Haircut (#388) | 8/9 | 6/6 | 6/6 | 8/9 | 6/6 | 6/6 | 6/6 | 6/6 | 6/6 | | | | | 6/6 | 6/6 | 6/6 |
| Get dressed for Day (#128) | 8/9 | 6/6 | 6/6 | 8/9 | 6/6 | 6/6 | 6/6 | 6/6 | 6/6 | | | | | 5/31 | 6/6 | 6/6 |
| Go to Dairy Queen (#384) | 8/9 | 5/31 | 6/6 | 8/9 | 6/6 | 6/6 | 6/6 | 6/6 | 6/6 | | | | | 5/31 | 6/6 | 6/6 |
| Go to Movie (#376) | 8/9 | 6/6 | 6/6 | 8/9 | 6/6 | 6/6 | 6/6 | 6/6 | 6/6 | | | | | 6/6 | 6/6 | 6/6 |
| Go to State Fair (#401) | 8/9 | 6/6 | 6/6 | 8/9 | 6/6 | 6/6 | 6/6 | 6/6 | 6/6 | | | | | 5/31 | 6/6 | 6/6 |
| Groom Self (#338) | 8/9 | 6/6 | 6/6 | 8/9 | 6/6 | 6/6 | 6/6 | 6/6 | 6/6 | | | | | 6/6 | 6/6 | 6/6 |
| Healthy snack Shopping (#403) | 8/9 | 6/6 | 6/6 | | 6/6 | 6/6 | 6/6 | 6/6 | 6/6 | | | | | 6/6 | 6/6 | 6/6 |
| Hike in Park (#390) | 8/9 | 6/6 | 6/6 | 8/9 | 6/6 | 6/6 | 6/6 | | 6/6 | | | | | 5/31 | 6/6 | 6/6 |
| Load Dishwasher (#405) | 8/9 | 6/6 | 6/6 | | 6/6 | 6/6 | 6/6 | 6/6 | 6/6 | | | | | 6/6 | 6/6 | 6/6 |
| Make Treat (#389) | 8/9 | 6/6 | 6/6 | | 6/6 | 6/6 | 6/6 | 6/6 | 6/6 | | | | | 5/31 | 6/6 | 6/6 |
| Monitor Outing behavior (#822) | | | | | | | | | | | | | | 9/10 | | |
| Monitor for Self Injury (#119) | 8/9 | 5/31 | 6/6 | 8/9 | 6/6 | 6/6 | 6/6 | 6/6 | 6/6 | | | | | 5/31 | 6/6 | 6/6 |
| Monitor for Wearing mouth guard (#7) | 8/9 | | 7/22 | 8/9 | | | | | | | | | | | | |

📝 Qualify Selected Cells   ✗ Cancel/Restart   ✓ Save Worksheet   🚪 Quit/Finished 🚫 DisQualify Selections

Staff Display:

Client Schedule Butt | Staff Schedule: JEA | Today: Monday, 6/28/99

KCB — Hourly Data Requir
DLC — Hourly Data Requir
RJL — Hourly Data Requir
DLH — Hourly Data Requir
MCR — Hourly Data Requir
East Reviewing Training Needs | ✓ Show Completed | Show Yesterday | Log Out

- A  RJL  4p:  Afternoon Rountine
- A  MCR  4:05p:  Leisure/Errand Community Outing
- A  JEA  Shop for Personal Items
- A  JEA  Hang Coat
- A  RJL  4:35p:  Community Leisure/Errand
- A  MCR  5p:  Dinner
- A  RJL  5p:  Dinner
- A  RJL  5:20p:  Cognitive/Academic
- A  RJL  5:40p:  Medical Procedures
- A  RJL  5:55p:  Snack/Drink
- A  MCR  6p:  Choose Activity
- A  MCR  6:50p:  Medical Procedures
- A  RJL  7:05p:  At Home Leisure/Hobbies
- A  MCR  7:10p:  Exercising
- A  MCR  7:40p:  Toileting
- A  MCR  7:50p:  Evening Leisure/Hobbies
- A  MCR  8:05p:  Prepare for Work Next Day Monitoring/As Needed Duties for MCR

- Prepare for Bath (#12)
- Bathe Self (#18)
- Get dressed for Day (#21)
- Monitor for Property Destruction (#35)
- Chart HPNs (#41)
- Hang Coat (#59)
- Wipe Mouth (#147)
- Shave Face (#149)
- Use Toilet (#149)

Finished

Fig. 24

Daily Assignment for: GES | Reassign | Print | Auto Close

MCG: Use Schedule Board

Method/Reinforcement:

Materials: schedule board, symbols
Reinforcement: The final activities on the board at this time (meal or restaurant) are excepted to reinforce use of the schedule board.

Procedural Issues/Notes:

Only pair set table with meal symbol, bathroom symbol with restaurant symbol. Set table and Bathroom symbol are on the top row and the other two symbols are on the bottom row. Only give physical prompting after 30 seconds.

This program will be implemented on Friday for restaurant night and Tuesday for the 7:30 PM meal.

Overview/Rationale:

Mary has learned several new symbols over the past several months. The objective is to provide Mary with a schedule board that can be used through out her day so she can anticipate upcoming events. The schedule board is designed to be in a choice format to provide her a way to communicate preferences.

Revisions/Planning:

Add additional activity options to the schedule. Add to the number of choices on the board.

Task Steps | Special Notes

✓ Finished

Fig. 25

MCG: Use Schedule Board  
Priority: High

Staff Assignment: MLA  
Nominal Time: 12p

PROCEDURAL ISSUES/NOTES:

Only pair set table with meal symbol, bathroom symbol with restaurant symbol. Set table and Bathroom symbol are on the top row and the other two symbols are on the bottom row. Only give physical prompting after 30 seconds.

This program will be implemented on Friday for restaurant night and Tuesday for the 7:30 PM meal.

METHOD/REINFORCEMENT:

Materials: schedule board, symbols  
Reinforcement: The final activities on the board at this time (meal or restaurant) are expected to reinforce use of the schedule board.

TASKS:

| -Assn.- | Task Statements, (Note: •=Data required, and ¶=Acceptable prompt) |
|---|---|
| -- | When schedule board is set up, give the cue "Let's check your schedule." |
| CLIENT | When given cue, go to the schedule board. |
| | • P-E-R-F-O-R-M-A-N-C-E:  -0-  -1-  -2-  -3-  -4-  -5- |
| | (¶a:  Point to board) |
| | (¶b:  Take her hand and wa ) |
| -- | When at the schedule board, give the cue "Time for ___" (insert activity). |
| CLIENT | When given cue, pull off one symbol from the top row. |
| | • P-E-R-F-O-R-M-A-N-C-E:  -0-  -1-  -2-  -3-  -4-  -5- |
| | (¶a:  Point to top row) |
| CLIENT | After pulling off the symbol, hand it to the instructor. |
| | • P-E-R-F-O-R-M-A-N-C-E:  -0-  -1-  -2-  -3-  -4-  -5- |
| | (¶a:  With prolonged gestu) |
| | (¶b:  Guide hand to your p ) |
| -- | When symbol is pulled, extend open palm until symbol is placed in it. |
| CLIENT | After cue, access the activity. |
| | • P-E-R-F-O-R-M-A-N-C-E:  -0-  -1-  -2-  -3-  -4-  -5- |
| | (¶a:  Point to activity lo) |
| | (¶b:  Take her hand and wa ) |
| -- | When receiving the symbol, say "Okay, let's ___" (insert activity) |
| -- | Once the activity has been completed, give cue "Let's check your schedule." |
| CLIENT | When given cue, go to the schedule board. |
| | • P-E-R-F-O-R-M-A-N-C-E:  -0-  -1-  -2-  -3-  -4-  -5- |
| | (¶a:  Point to board) |
| | (¶b:  Take her hand and wa ) |
| -- | When at the schedule board, give the cue "Time for ___" (insert activity) |
| CLIENT | When given cue, pull off one symbol from the bottom row. |
| | • P-E-R-F-O-R-M-A-N-C-E:  -0-  -1-  -2-  -3-  -4-  -5- |
| | (¶a:  Point to bottom row) |
| CLIENT | After pulling off the symbol, hand it to the instructor. |
| | • P-E-R-F-O-R-M-A-N-C-E:  -0-  -1-  -2-  -3-  -4-  -5- |
| | (¶a:  With prolonged gestu) |
| | (¶b:  Guide hand to your p ) |
| -- | When symbol is pulled, extend open palm until symbol is placed in it. |
| -- | When receiving the symbol, say "Okay, let's ___" (insert activity) |
| CLIENT | After cue, access the activity. |
| | • P-E-R-F-O-R-M-A-N-C-E:  -0-  -1-  -2-  -3-  -4-  -5- |
| | (¶a:  Point to activity lo) |
| | (¶b:  Take her hand and wa ) |

Scales: Performance
  0. no opportunity
  1. did not participate
  2. staff assistance: you had to do part of it
  3. heavy prompting: many gestures or cues
  4. minimal prompting: some assistance to focus
  5. integrated: competent; no "artificial" support, quality outcome

Daily Report: NCD: Thursday, 09/02/1999

| Sched | Date/Time | Entry | Date/Time | Person: | Duty |
|---|---|---|---|---|---|
| 3:00p | (09/02) | 3:51p | (09/02) | ----: | Read Communication Book (#1963) |
| 3:00p | (09/02) | 5:49p | (09/02) | ----: | Check Community Event Calendar (#2303) |
| 3:00p | (09/02) | 5:42p | (09/02) | ----: | Person In Charge (E) (#1619) |
| 3:00p | (09/02) | 7:26p | (09/02) | MCR: | "TAKE AND PUT IT HERE" (#2309) |
| 3:00p | (09/02) | 5:49p | (09/02) | MCR: | Wipe Mouth (#160) |
| 3:00p | (09/02) | 7:25p | (09/02) | ----: | TAKE RADIO/CELL PHONE (#2215) |
| 4:00p | (09/02) | 5:50p | (09/02) | MCR: | Fade juice/Drink water (#2177) |
| 4:00p | (09/02) | 7:30p | (09/02) | MCR: | Count money in wallet (#1426) |
| 4:00p | (09/02) | 5:45p | (09/02) | MCR: | TOILETING REINFORCER (#1936) |
| 4:05p | (09/02) | 5:57p | (09/02) | MCR: | Look at Magazines (#213) |
| 4:05p | (09/02) | 7:24p | (09/02) | MCR: | Choose Transitional Object (#131) |
| 4:10p | (09/02) | 3:51p | (09/02) | MCR: | Relax in chair (#210) |
| 4:30p | (09/02) | 7:31p | (09/02) | MCR: | TOILETING REINFORCER (#1936) |
| 4:37p | (09/02) | 5:47p | (09/02) | MCR: | EXAM ROOM DESENSITIZATION 2 (#2082) |
| 5:00p | (09/02) | 5:47p | (09/02) | MCR: | Quik making (#175) |
| 5:00p | (09/02) | 7:30p | (09/02) | MCR: | Eat Dinner (#385) |
| 5:01p | (09/02) | 5:48p | (09/02) | MCR: | Set Table (#188) |
| 5:10p | (09/02) | 7:34p | (09/02) | MCR: | Wipe Mouth (#160) |
| 6:00p | (09/02) | 6:07p | (09/02) | MCR: | Take Break (#1590) |
| 6:00p | (09/02) | 7:25p | (09/02) | ----: | PIC 6pm (E) (#1732) |
| 6:00p | (09/02) | 5:48p | (09/02) | MCR: | Gospel Songs (#182) |
| 6:05p | (09/02) | 7:28p | (09/02) | MCR: | Ball Toss (#187) |
| 6:15p | (09/02) | 5:49p | (09/02) | MCR: | TOLERATE NAIL FILE (#2251) |
| 6:30p | (09/02) | 6:08p | (09/02) | MCR: | Read to Marlo (#183) |
| 6:45p | (09/02) | 7:30p | (09/02) | MCR: | Conditioned Reinforcer (#184) |
| 7:00p | (09/02) | 7:31p | (09/02) | MCR: | TOILETING REINFORCER (#1936) |
| 7:30p | (09/02) | 7:26p | (09/02) | MCR: | Weigh on scale (#176) |
| 7:54p | (09/02) | 7:27p | (09/02) | MCR: | Med Desensitization Procedure (#132) |
| 8:00p | (09/02) | 8:29p | (09/02) | MCR: | Make juice (#173) |
| 8:05p | (09/02) | 9:41p | (09/02) | MCR: | Brush teeth (#100) |
| 8:10p | (09/02) | 9:41p | (09/02) | MCR: | Put Pajamas on (#157) |
| 8:30p | (09/02) | 9:41p | (09/02) | ----: | PIC 9pm (E) (#1871) |
| 8:30p | (09/02) | 8:28p | (09/02) | MCR: | Chart in Day Program Book (E) (#1713) |
| 8:30p | (09/02) | 7:34p | (09/02) | MCR: | Chart Community Access (#2120) |
| 8:30p | (09/02) | 8:27p | (09/02) | MCR: | Chart in HPN's (#1708) |
| 8:30p | (09/02) | 9:41p | (09/02) | RJL: | SLEEP PROCEDURE (#2263) |
| 8:30p | (09/02) | 8:33p | (09/02) | MCR: | Count money in wallet (#1426) |
| 9:00p | (09/02) | 8:29p | (09/02) | ----: | Straighten bathroom closets (#1397) |
| 9:00p | (09/02) | 8:29p | (09/02) | ----: | Clean mirrors (#1395) |
| 9:00p | (09/02) | 8:29p | (09/02) | ----: | Clean Refridgerator (#2312) |
| 10:30p | (09/02) | 10:41p | (09/02) | DLC: | Appropriate smoking (#1060) |

UNFINISHED DUTIES:

6:00p (09/02) MCR: TOILETING REINFORCER (#1936)
Please explain: *he refused*

6:10p (09/02) MCR: DESENSITIZE TO DOORWAYS (#2342)
Please explain: *scheduling conflict*

Certification: I have performed the above duties as listed or I have given a reason why not. Additionally, I have completed my assigned Hourly Monitoring/Intervention duties Signature: *Nora C. Ditto*  9 / 2 / 99
Direct-Care Person: NCD

STANDARDIZED INFORMATION MANAGEMENT SYSTEM FOR LONG-TERM RESIDENCE FACILITIES

FIELD OF THE INVENTION

The present invention relates generally to the field of information management systems. More specifically, the present invention relates to a standardized information management system for long-term residence facilities, such as group homes for people with disabilities, nursing homes and the like, that monitors and promotes consistency, stability, and improvement in the care, tracking and teaching of the clients of the facility. Most important, the present invention provides a structure for continual improvement of the quality of individual service delivery and the enhanced living options for each client.

BACKGROUND OF THE INVENTION

The use of computer technology in the field of health care has grown extensively over the last two decades. Today, computers are routinely used in hospital and clinical settings as critical components of health care delivery. One important area of health care where computers have been utilized in the delivery of health care services is in the area of monitoring and tracking of patient information.

Computer-based devices that include sensors or other equipment for taking patient measurements as part of a health monitoring system are shown, for example, in U.S. Pat. Nos. 4,803,625, 5,199,439, 5,307,263, 5,372,709 and 5,558,638. U.S. Pat. No. 5,691,215 describes a system for monitoring and generating reports and trend analysis based on daily living activity monitored by use of motion detectors or similar activity detection subsystems. Health monitoring systems that use computers as patient input devices for collecting and tracking data entered by a patient are shown, for example, in U.S. Pat. Nos. 5,542,420 and 5,890,997. The processing of accounting and insurance information in a hospital or clinic are typically managed by computer systems, as shown, for example, in U.S. Pat. Nos. 5,732,401 and 5,799,286. Patient data may even be directly entered into a computer by the physician or care provider, as shown, for example, in U.S. Pat. No. 5,845,253 that describes a system in which a physician enters patient data which is then archived and tracked longitudinally, and U.S. Pat. No. 5,691,932 that describes a care giver data collection and reminder system for use particularly with infants.

While the use of computer systems in a hospital or clinical setting to monitor and track patient information in the delivery of health care services has become widespread, there has not been a corresponding utilization of computer technology in monitoring and tracking information about the clients of long-term residence facilities, such as group homes for people with disabilities, mental health facilities, juvenile justice facilities, nursing homes, traumatic brain injury facilities and the like. There are many potential reasons why computer systems have not been adapted for use in such long-term residence facilities. Unlike clinical and hospital settings that offer health care services designed to return a patient to normal health, long-term residence facilities provide life care services designed to support and maintain a client's normal daily living activities. Although these kind of life care services involve unique hands-on, one-on-one services that can only be delivered by individual staff members, these services are relatively simple from a technology perspective when compared to the high technology, equipment-oriented services involved in many kinds of health care services. Instead of being funded primarily by private insurance reimbursements like most hospital and clinics, long-term residence facilities more typically have limited financial resources that do not permit experimentation with the use of expensive computer technology. To complicate matters further, many of the clients of these long-term residence facilities may have limited capacities to communicate with staff about their physical and emotional well-being. This can make even normal communications difficult and the use of client-controlled computer interfaces almost impossible. Collecting information about one aspect of a patient's life that is the focus for specific health care services can be a manageable job; however, data collection and management in a long-term residence facility is a formidable job because it would need to be continual and practically all-encompassing. For these reasons and others, there has been no comprehensive and systematic approach to the utilization of computer technology and information management systems in long-term residence facilities.

SUMMARY OF THE INVENTION

The present invention is a standardized information management system for use in long-term residence facilities that continually collects and manages all information related to both the clients and staff of the facility. The collection and management of this information is standardized to create consistency and stability in the care, tracking and teaching of the clients of the facility. To facilitate this standardization, the information management system breaks activities of the clients down into a set of defined duties, each of which represent a unit of assignable work that involves a client, a staff member or both. The step-by-step tasks that comprise a given duty are individually definable using a standardized database process that structures the definition of each task within certain parameters and provides a reusable set of resources once the tasks are created in the system. Duties may be clustered together to form activities which are then scheduled as staff responsibilities based on staff availability and qualifications and appropriateness to client needs and preferences. A comprehensive plan for each client is created by scheduling relevant activities for that client on a daily basis. The plan is displayed for staff members at a centrally located work station by the system and the performance of each duty may be evaluated and recorded in the system using standardized rating scales and special data collection set-ups as appropriate. The system also allows for recording of periodic information on health and behavior management issues in real time. All of this information is compiled by the system for analysis to generate standardized and customized reports that provide feedback to the staff for purposes of future planning and the dissemination of data summaries to external stakeholders of the long-term residence facility for informational and monitoring purposes.

The information management system is implemented as part of a networked computer system that runs three sets of software processes: (1) the utility processes for managing personnel records and work shift schedules, including the master scheduler, (2) the supervisory processes for planning service needs and posting daily schedules, including the individual planner process, the task definition process, and the assessment process, and (3) the display processes including the kiosk display processes that operates a display device located in the living area of a facility for displaying current work information and entering data into the system. Together, these process modules implement the major features of the standardized information management system of the present invention, including: (i) creating, defining and scheduling activities for both staff and clients; (ii) maintaining staff qualifications and availability for scheduling qualified staff to perform activities; (iii) displaying information and tracking performance of scheduled activities; (iv) completing periodic data entry on health and behavioral issues for the clients; and (v) generating a variety of flags, reports and graphs based on a compilation and analysis of all of this information.

One of the major hardware components of the preferred embodiment of the information management system of the present invention is a kiosk display networked into the computer system and located in the living quarters of the long-term residence facility. Staff can use the kiosk to obtain information from, and enter data into, the system while they are working with the clients. Preferably, the kiosk display is provided with a touch screen display where the touch screen may be protected from access by the clients if necessary to prevent damage or inappropriate access.

The present invention is a comprehensive and systematic approach to providing information management services in the context of a long-term residence facility. By adopting the standardized approach to the definition, assignment, tracking and reporting of all of the daily duties and activities of both the clients and staff, the present invention affords the opportunity for consistency and stability in client-staff interaction. The same tasks will be performed in the same way with each client, regardless of which staff member is delivering these life services. The same set of rating scales are used to evaluate performance, making it possible to statistically evaluate performance in terms of reliability, integrity and validity. The use of standardized data definitions across a broad range of tasks and clients offers the opportunity for practical applications of psychological research. This can be accomplished through the clustering of tasks into basic skill sets. Such applied psychological research will enable greatly improved professional planning for skill enhancement programs for dependent clients.

The continual and standardized tracking of performance of activities and duties of the clients, as well as health and behavioral information, affords the opportunity to provide meaningful feedback on the effectiveness of the life services being provided. This feedback is not only useful for the staff at the facility, but also can be provided to a wide variety of concerned third party stakeholders, including health care providers, guardians and families, and licensing and regulatory authorities. The ease of use of the kiosk display together with the standardized scales used to evaluate clients encourages highly accurate data collection on a real time basis. Moreover, the standardized information management system is comprehensive and is organized to encompass all of the major aspects of providing life care services for long-term residence facilities such that staff confusion over where to find or record information is eliminated. In contrast to the burdensome and relatively ineffective nature of the existing disparate methods of information collection utilized in long-term residence facilities, the standardized information management system of the present invention actually assists staff in their job of providing life care services to the clients of a long-term residence facility.

BRIEF DESCRIPTION OF THE DRAWINGS

FIGS. 2–5 are examples of various reports generated by the information management system of the present invention for third party stakeholders.

FIG. 7 is an example of a screen entry for entering information in the personnel registry database.

FIG. 8 shows the vehicle reservation screen.

FIG. 9 is an example of the screen displaying the Planned Activities Tree.

FIG. 10 is an example of a screen displaying the Supporting Services Tree.

FIG. 11 is an example of a screen showing an assignable direct care duty setup.

FIGS. 12 and 13 show examples of two different screens utilized in setting up a task.

FIG. 15 is an example of a screen showing the assignment of duties to staff.

Figure 16:
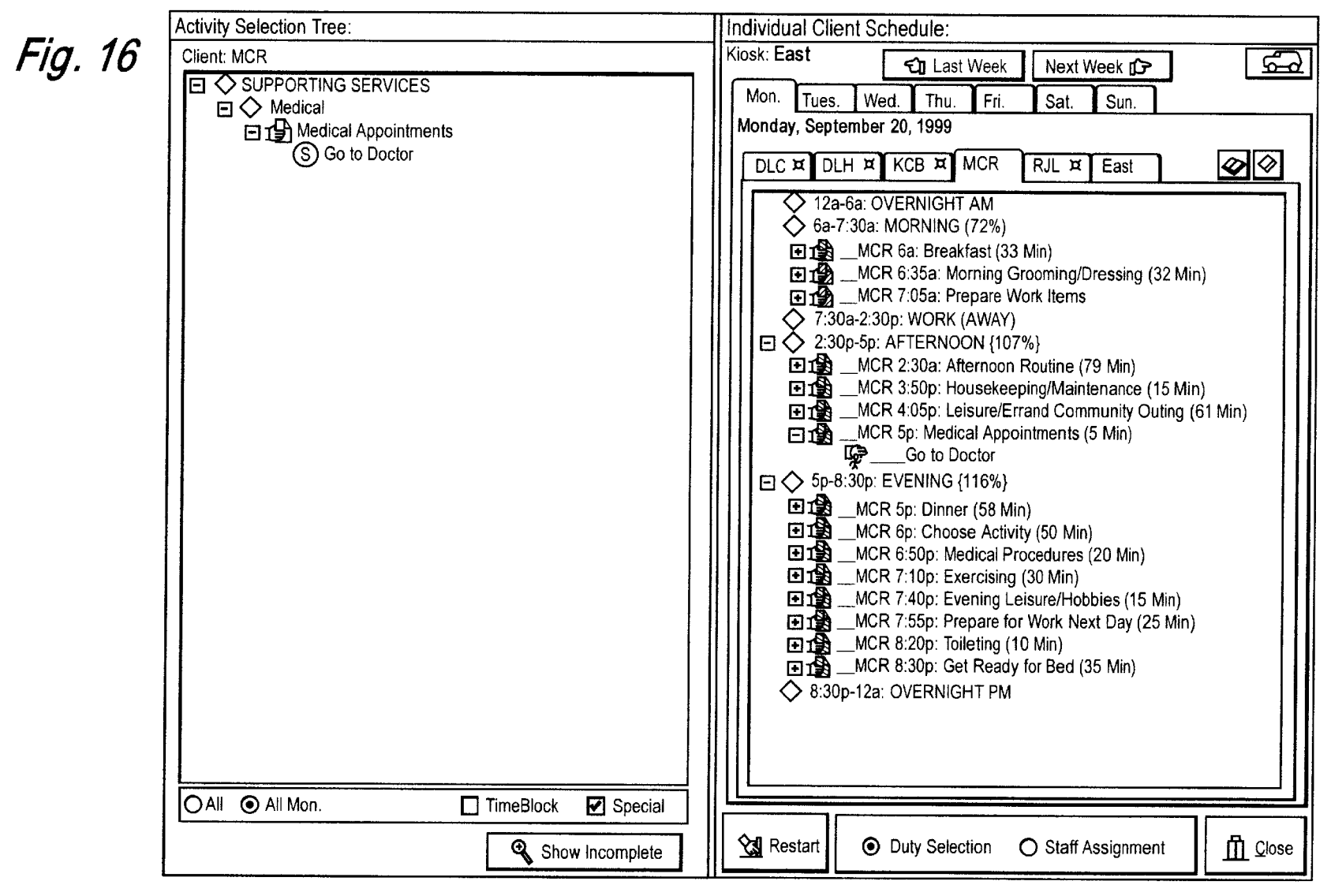

FIG. 16 is an example of the activity selection process.

FIG. 17 shows the Program Training Records tracking screen.

FIG. 18 is an example of the screen display alerting staff of current training needs.

FIG. 19 is an example of the special data setup to generate a report.

FIGS. 22–29 are examples of screen displays at the kiosk as utilized by staff members and several kiosk print outs.

DESCRIPTION OF THE PREFERRED EMBODIMENT

As used within the present invention, the term long-term residence facility encompasses group homes for people with disabilities, mental health facilities, nursing homes, traumatic brain injury facilities and the like. Unlike clinical and hospital settings that offer health care services designed to return a patient to normal health, long-term residence facilities provide life care services designed to support and maintain a client's normal daily living activities and developmental opportunities for extended periods of time, typically months or years. In a long-term residence facility, the life care services are provided because the clients are generally incapable of performing normal daily living activities without such assistance. In addition, many of the clients of these long-term residence facilities may have limited capacities to communicate with staff about their physical and emotional well-being that will restrict their ability to actively participate in the process of evaluating their life care services.

Although the description of the preferred embodiment of the present invention will be presented in terms of application of the standardized information management system to a group home for children and adults with autism, it will be recognized that the details of present invention specific to the needs of dependent individuals with autism can be modified to address the specialized needs of other target groups of long-term clients without departing from the basic processes of the present invention. It will also be recognized that many of the aspects of the present invention are equally applicable to an information management system for long-term rehabilitation facilities, such as juvenile justice facilities, half-way homes, chemical dependency programs and the like. While the clients of such long-term rehabilitation facilities may not be dependent upon the life care services provided at these facilities to meet their daily living needs, the present invention is well suited for the similar requirements of these long-term rehabilitation facilities to provide a structured and monitored living environment for their clients.

Figure 1:
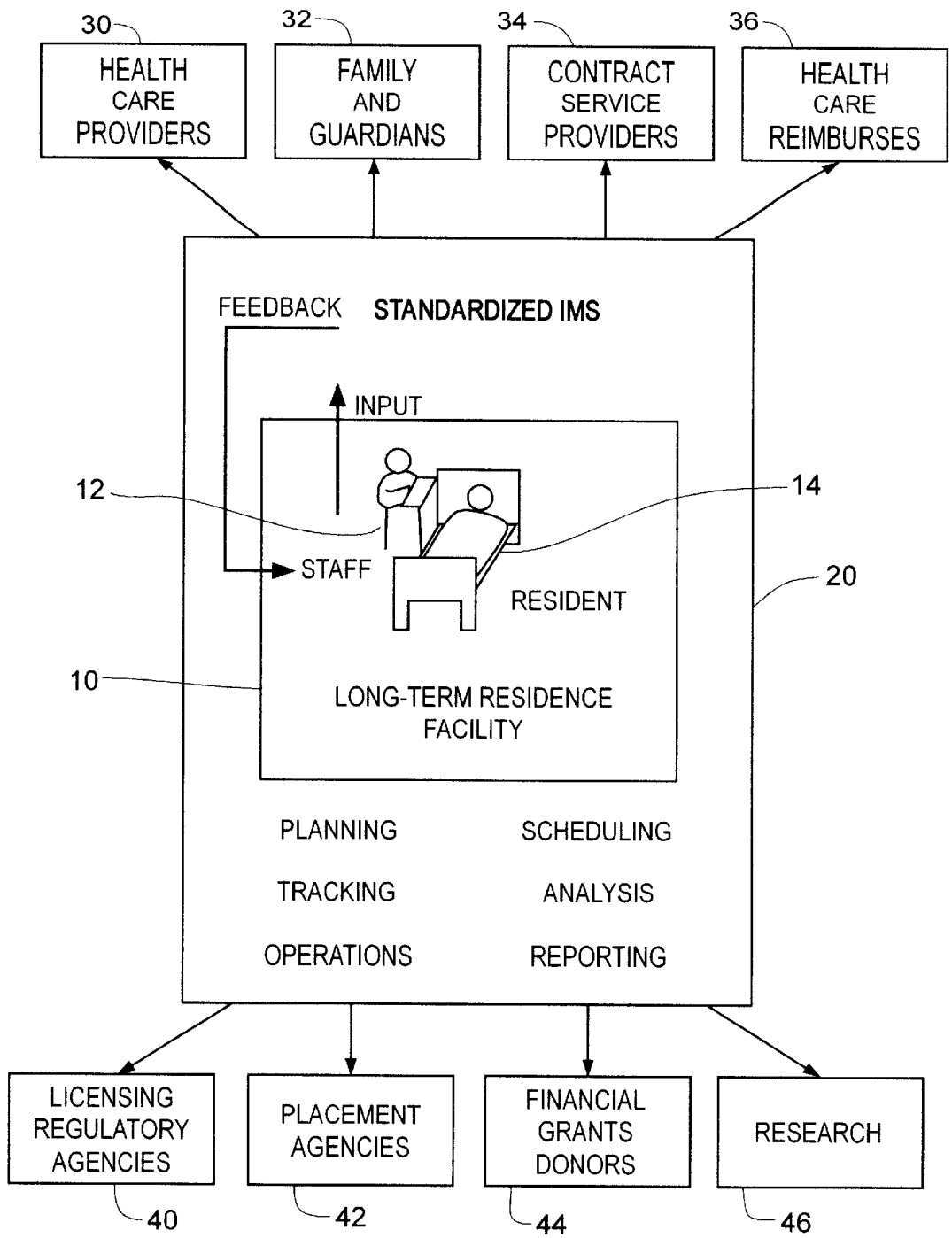
FIG. 1 is an overall block diagram of the ideal information flow for a long-term residence facility.

Referring to FIG. 1, an ideal flow of information among the various third party stakeholders of a long-term residence facility 10 is shown. The primary information flow managed by the standardized information management (SIM) system 20 is between staff members 12 and clients 14. As will be described hereinafter in greater detail, the SIM system 20 can accomplish a variety of functions internal to the long-term residence facility 10, including planning, scheduling, tracking, analysis, management of operations and reporting. The system 20 also reports and provides information to a variety of third parties stakeholders external to the long-term residence facility 10. The information required for all stakeholders arises from the moment-to-moment activities of the direct-care staff members who share the daily lives of dependent individuals providing them with the help they require to live. Specifically, the hundreds of daily acts that these staff members make in pursuing their duties mark the differences between services that are satisfactory to all parties or to none.

Figure 2:
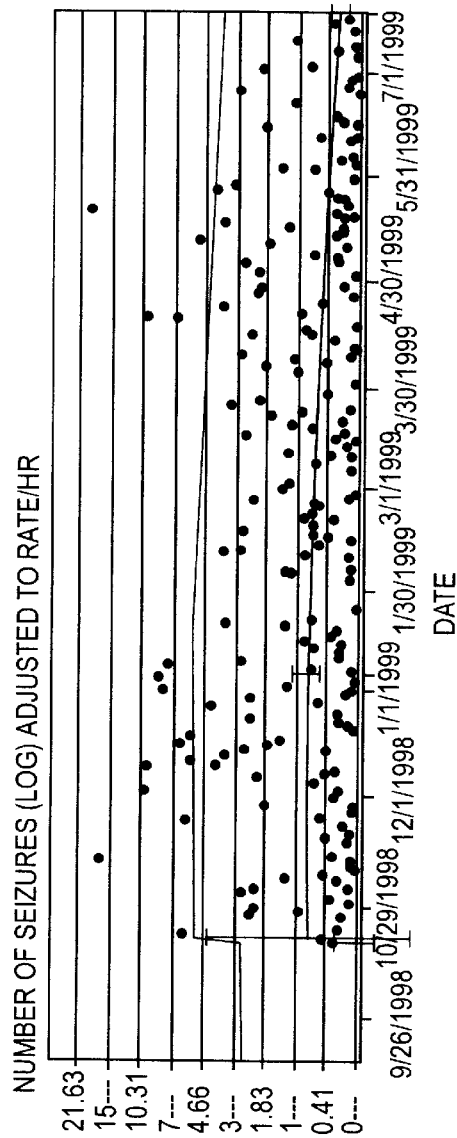

Health care providers 30 can benefit greatly from the SIM system 20 in the treatment and management of the health care issues for the clients 14. By longitudinally tracking health and behavioral issues and reporting these as a function of changes in medication, as shown for example in FIG. 2, it is much easier for a health care provider to evaluate whether a given medication or treatment is proving effective for a particular client. This type of information is particularly valuable in cases where the client has a limited capacity to report their physical and emotional well being. Preferably, such a report provides a graphic presentation of the tracked health and/or behavioral data over time and allows for derivation of statistical significance of the variables being evaluated.

Family and guardians 32 can be provided with periodic reports detailing the life care services being provided for a client, as shown for example in FIGS. 3 and 4. These kind of reports can greatly ease concerns over the quality of service. The reports also can be the basis for constructive feedback from family and guardians 32 to the staff 12 on certain issues identified in these reports, such as how a client's history may be impacting on an issue related to their life care services. Contract service providers 34, such as job programs, day care providers, transportation providers, program specialists and the like, also can be provided with similar types of up-to-date information relevant to the services that are being contracted. In the case of group homes for people with disabilities, for example, it is typical for the clients to have a job with a development center, for example, which the clients attend during the day.

With respect to licensing and regulatory authorities 40 and placement agencies 42, one important feature of the SIM system 20 of the present invention is the ability to provide more frequent and more effective evaluations and assessments of a client than the current practice of providing relatively subjective evaluations on an annual basis. An example of this kind of report tracking daily evaluations of a client is shown in FIG. 5. The system 20 is capable of customizing such reports to the individual requirements of a given authority 40 or agency 42. Because the reports utilize evaluations based on a standardized reporting scale, as described in more detail hereinafter, licensing and regulatory authorities, as well as placement agencies, are given an increased level of confidence in the performance of a long-term residence facility 10 and the life care services being provided to the clients 14 of that facility.

Other third party stakeholders can also be provided with information and reports generated by the SIM system 20, including financial grants and donors 44 and research institutions 46. In these cases, it is important that the system 20 is able to customize reports and information based on all of the various information tracked by the system. The SIM system 20 offers research institutions, for example, a level of quality of information on clients of long-term facilities 10 that has not been available until now. Whether the research is medical science or social science, the standardized reporting and standardized scales of the SIM system 20 allow reliable statistical evaluations to be undertaken for the variables being evaluated.

Figure 6:
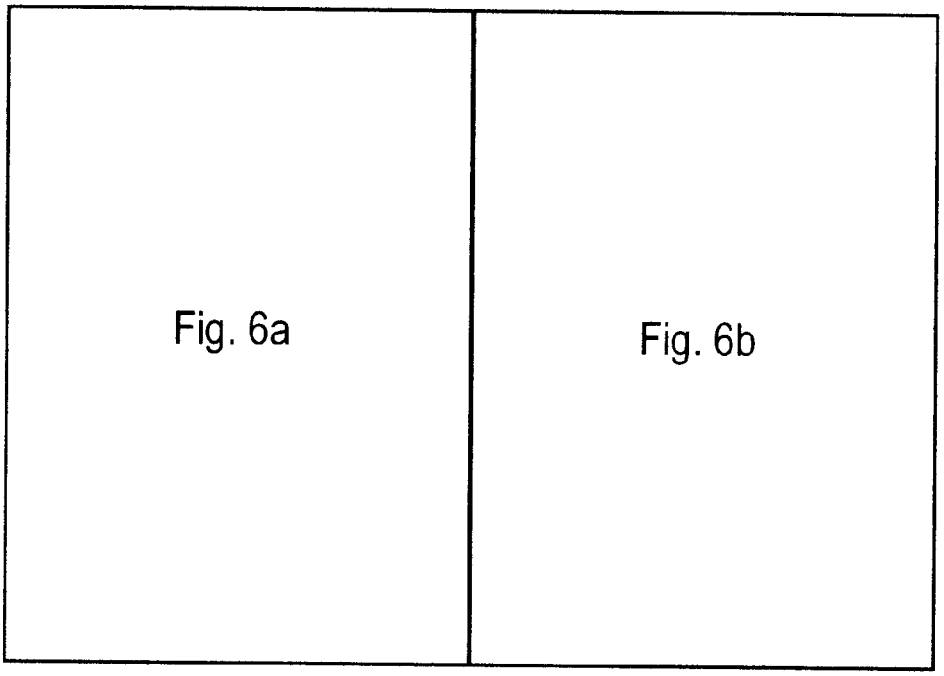
FIG. 6 is an overall block-state diagram of the principal modules, processes and databases of the preferred embodiment of the present invention.
Figure 6A:
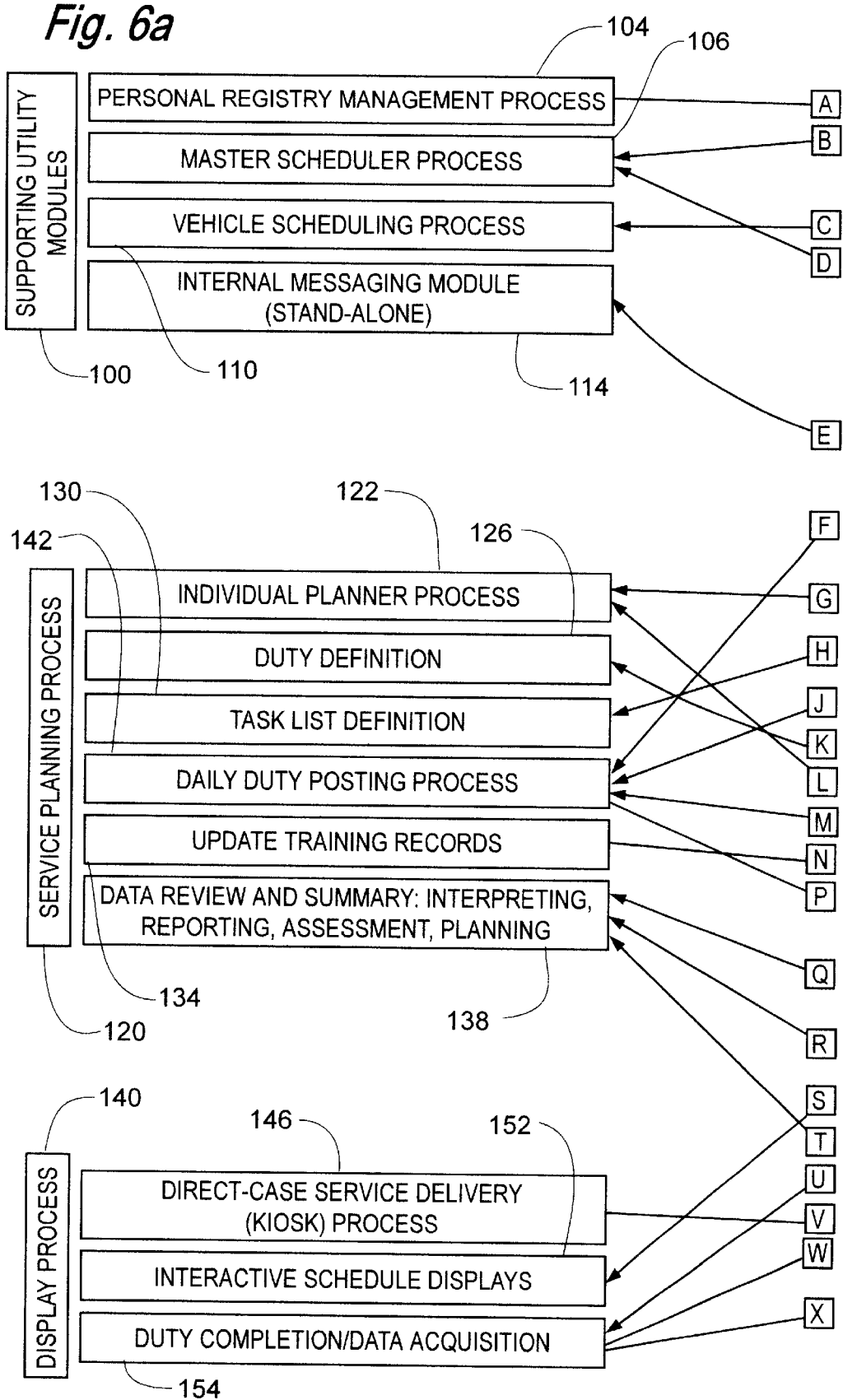
Figure 6B:
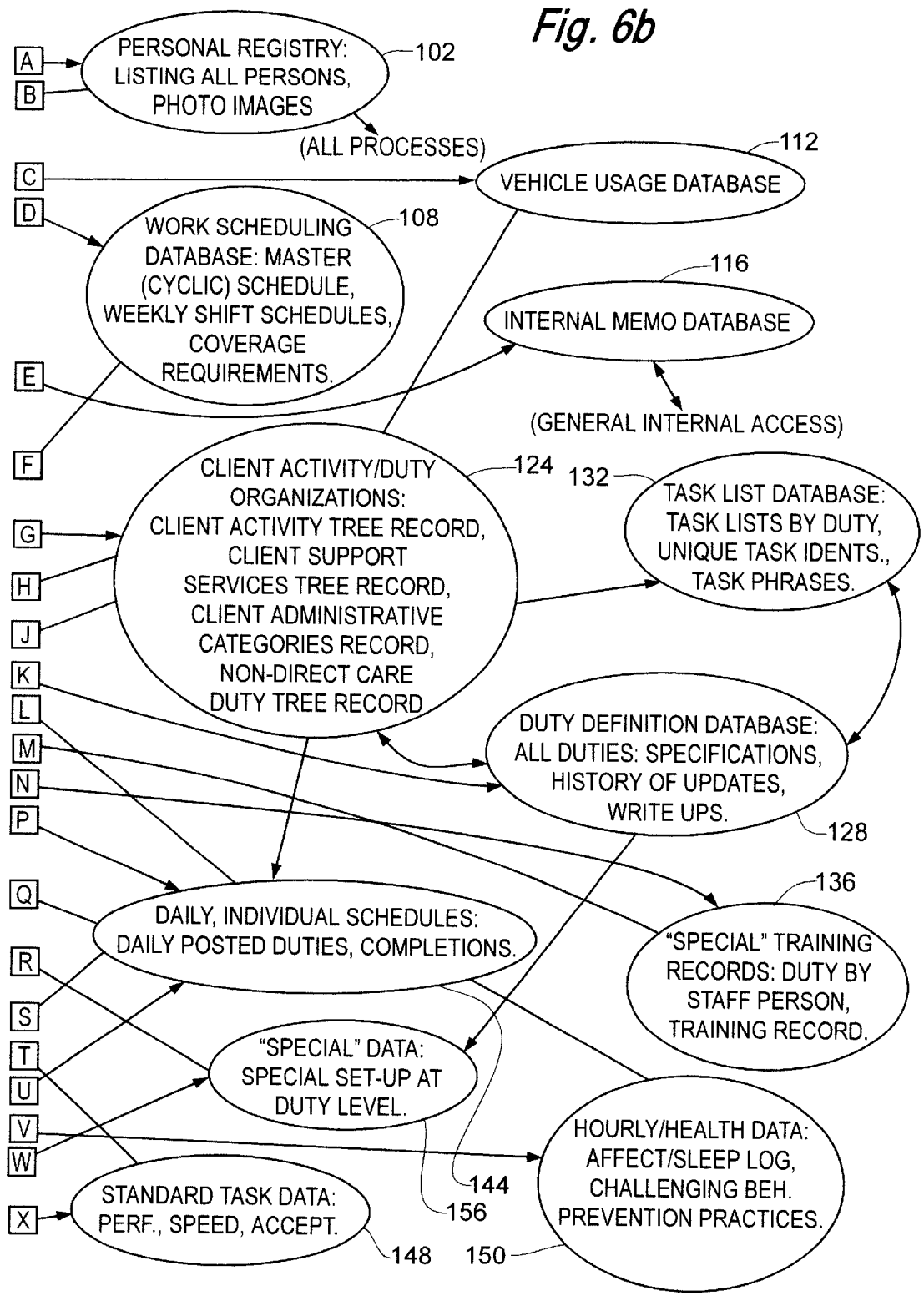

Referring now to FIG. 6, an overall block-state diagram of the three major processes of the preferred embodiment of the present invention is shown. The three major processes are the utility processes 100, the supervisory processes 120, and the display processes 140. Each of these processes will be described in terms of their component parts and the various databases that interact with these processes. It should be understood that the SIM system 20 of the present invention is intended to be implemented on a networked computer system, preferably consisting of two or more personal computers networked together and sharing access to common databases. The various processes 100, 120 and 140 have been programmed in Pascal and C++ in the preferred embodiment, although it will be recognized that the functions of these processes can be implemented in a variety of programming languages and database formats within the basic processes of the present invention. A simple but important part of the system is maintenance of a personnel registry database 102. Each person who is a staff member at the particular long-term residence facility is uniquely identified in this database 102 with a code (usually, the person's initials). Some of his or her employment status data is made available to the system for purposes of identification, position, and relevant qualifications. Identification photographs may also -entered. Entry and maintenance of this information in the database 102 is managed by the personnel registry management process 104. The personnel registry management process 104 enables the personnel director and supervisors in each department to recognize deficiencies in training and to ensure that it is provided. It allows routine tracking of qualifications that require retraining/updating (e.g., CPR, evaluation schedules) on a consistent schedule.

Figure 7:
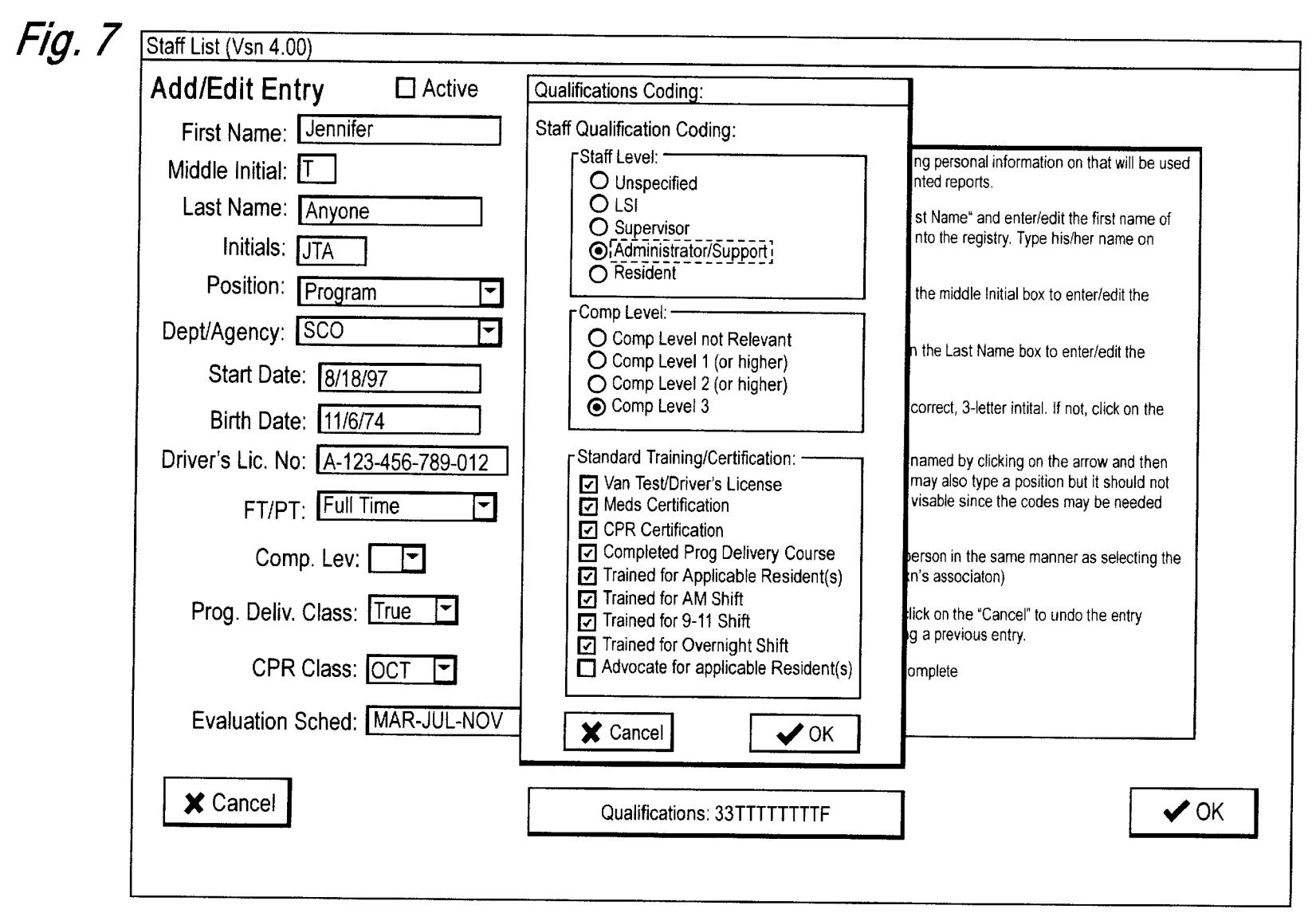

In a preferred embodiment of the data entry screen as shown in FIG. 7, the personnel registry database 102 includes the following identification information: Name (first, middle initial, last), Identification code (initials and/or number), Identification photo (approx. 2"×2" display), Position (Client, LSI, Coordinator, Manager, etc.), Department, and other miscellaneous information needed for personnel purposes. Additional information is maintained in the personnel registry database 102 related to personnel qualifications, including: General department training (for specific shifts and clients), Vehicle operation, Medication administration, CPR and completion of other required training modules. Preferably, a pull down menu with check boxes is used to indicate certain standard qualifications. An instruction window (shown in background) instructs a user who is not familiar with the requirements for completing this screen.

The Master Scheduler process 106 manages the work scheduling database 108 that contains the staff work schedules. Daily planning requires timely information about when staff are available to perform the direct-care duties. Reports and alerts generated from this process 106 permit the identification of staff shortages. The Master Scheduler process 106 provides organization and design assistance for setting up staffing requirements routine and daily staff scheduling, identifying shortages, and staffing summaries.

Other processes in the utility processes 100 include the vehicle scheduling process 110 which utilizes a corresponding vehicle usage database 112, and the internal messaging module 114 which utilizes an internal memo database 116 to implement e-mail like messages and notes within the system 20. In the case of the vehicle scheduling process 110, facility vehicles are scheduled for use from two places, the supervisor's computer and the kiosk. From the supervisor's computer, the supervisor schedules a vehicle while posting an outing or medical appointment for a client. From the kiosk, the staff review vehicle availability and schedule a time for outings as seen in FIG. 8. Recorded information includes date, time, department, and purpose.

It will be recognized that other types of utility processes could be added and/or customized depending upon the particular needs and clients of the long-term residence facility. For instance, if special facilities or equipment, such as a therapy room or a particular piece of diagnostic equipment, were utilized by the facility on a regular basis, scheduling processes and databases could be developed to incorporate the management of these into the system in a similar manner.

The second major set of processes are the supervisory processes 120 which are used by supervisory, management and planning personnel at a long-term residence facility 10 for planning, scheduling, tracking, analysis, management of operations and reporting functions. The Planner process 122 manages a large client database system 124 that incorporates information on all of the activities in which clients engage. Each activity represents a selective clustering of one or more defined duties suitable for a given client. Preferably, the activities are organized as a customizable list of client duties and supporting service needs in the form of a Planned Activity Tree and a Supporting Services Tree. The Planned Activity Tree includes the activities in which the client routinely engages. "Activities" are higher groupings of "duties" which organize an individual's day in sequential order. The duties within the Planned Activities Tree reflect the programming needs of the client, as well as the acquired skills. An example of a screen displaying the Planned Activities Tree is shown in FIG. 9. The Supporting Services Tree includes activities which are completed for the individual in order to maintain their safety and well-being; the client may not participate in the activity (i.e. monitor for self injury). An example of a screen displaying the Supporting Services Tree is shown in FIG. 10.

Each duty represents a unit of assignable work that involves a client, a staff member or both. A set of defined duties for each of a plurality of clients of the long-term residence facility are generated by a duty definition process 126 and maintained in a duty definition database 128. A duty is also a unit of work that can be assigned to direct-care staff. Each duty is a highly structured specification of what the client is to do and how staff are expected to support it and record relevant data for it. A duty contains all of the documents, staff qualifications or training requirements, prioritization and estimated time requirements needed to assign the unit of work. An example of a screen showing an assignable direct care duty setup for preparing cereal is shown in FIG. 11.

Preferably, each duty has a detailed "Task List" generated by a task definition process 130 and maintained in a task list database 132. The "Task List" spells out in detail what is to be done by both staff person and client for a given duty. The task list consists of logically ordered statements which are created within the process using a "user-friendly" process that facilitates the initial development of the list. Improvements based upon experience are edited into the task list where needed. While most duties involve both staff and clients, there are some non-client duties that do not involve client participation, such as distributing medication to stations and facility cleaning. FIGS. 12 and 13 show examples of two different screens utilized in setting up a task.

Preferably, as shown in FIG. 13, the task list will be created in a standardized process format selectively including the following:
 a. Condition ("When")
 b. Tool ("using")(optional)
 c. Action (verb phrase)
 d. Object (noun phrase)
 e. Criterion ("until")(optional)

A direct care duty is an aggregation of tasks for a particular client. By utilizing the standardized process to create task lists and then grouping these tasks lists hierarchically into duties and then into activities, a relatively straightforward and repeatable process is provided to dissect disparate behaviors of clients into collections of small teachable and trackable units.

Figure 14:
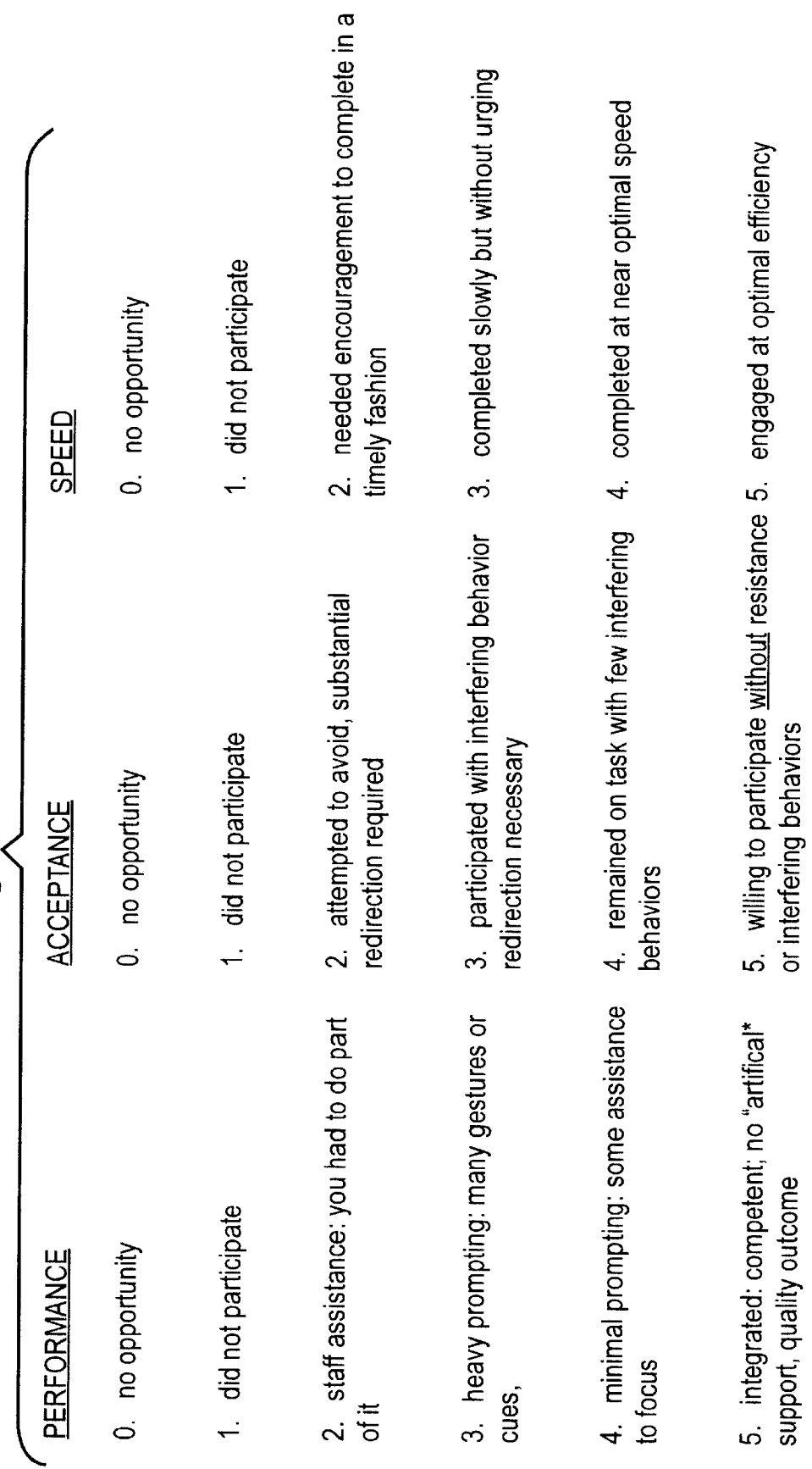
FIG. 14 is an example of three 5-point standardized rating scales.

An example of the structured organization of each duty would include:
 a. Classification for administrative uses: Comprehensive listing of all duties for a client indexed by category. Categories are used for organizational purposes and includes both Planned Activities and Supporting Services.
 b. Client identification: Each duty is client specific although a duty for one client may be used as a template for creating a similar duty for another client.
 c. Target kiosk: Each duty is assigned to a specific work area. The computer kiosk for the work area will display the assigned duties.
 d. Supplementary text that includes:
  1. Overview/Rationale: Why the task is being taught and the current level at which the client is engaging in that task/behavior. This provides a basis for comparison once formal instruction begins.
  2. Method/Reinforcement: List of materials needed to run the program/intervention. A reinforcer is specified to increase the likelihood that the learner will complete that task again.
  3. Procedural Issues/Notes: Specific information for staff is included here. For example, general guidelines for prompting or how to prepare program materials.
  4. Revisions/Planning: A plan is outlined to ensure that the task will be maintained and generalized to other duties involving the acquired task. Future plans to teach the client additional tasks within a duty are explained. Also, any program revisions will be documented and explained in this section.
 e. Update history: Maintains record of program revisions by documenting person, date, and purpose of update.
 f. Priority: Low (ex. Paint Picture), Medium, High (ex. Brush Teeth), Mandatory (ex. Pass Meds). Mandatory duties are time sensitive and must be completed as assigned.

g. Scheduling Options: Defines when a duty will appear on the Activity Tree for posting. Frequency, Days of week, and Time of day.

h. Time allotments: estimate of client and staff time required to complete duty i. Staff qualifications: Training required of staff to complete a duty may include the following: special training (duty specific), medication administration, vehicle operation, and CPR. Personnel Registry maintains the records.

j. Creation/Editing of Task List: Logically arranged statement of steps performed by staff or client. Expert design process leads user through writing of each task. Searching options scan database for previously defined tasks and task lists which may be "borrowed."

k. Assign Responsibilities (to tasks): Some tasks are performed by direct-care staff and others are performed by client.

l. Standard Data type selection: For tasks performed by client, data is required. Selection of three 5-point scales permitted: (1) performance, (2) speed, (3) acceptance. An example of these three 5-point scales is shown in FIG. 14.

m. "Special" database design and analysis set up: When a standardized scale is not appropriate, special data may be set up. For example, frequency data.

n. Hard-copy documentation: A print option exists at the kiosk and supervisor's computer. Staff can carry a hard copy to ensure consistency and reliable data collection.

Figure 15:
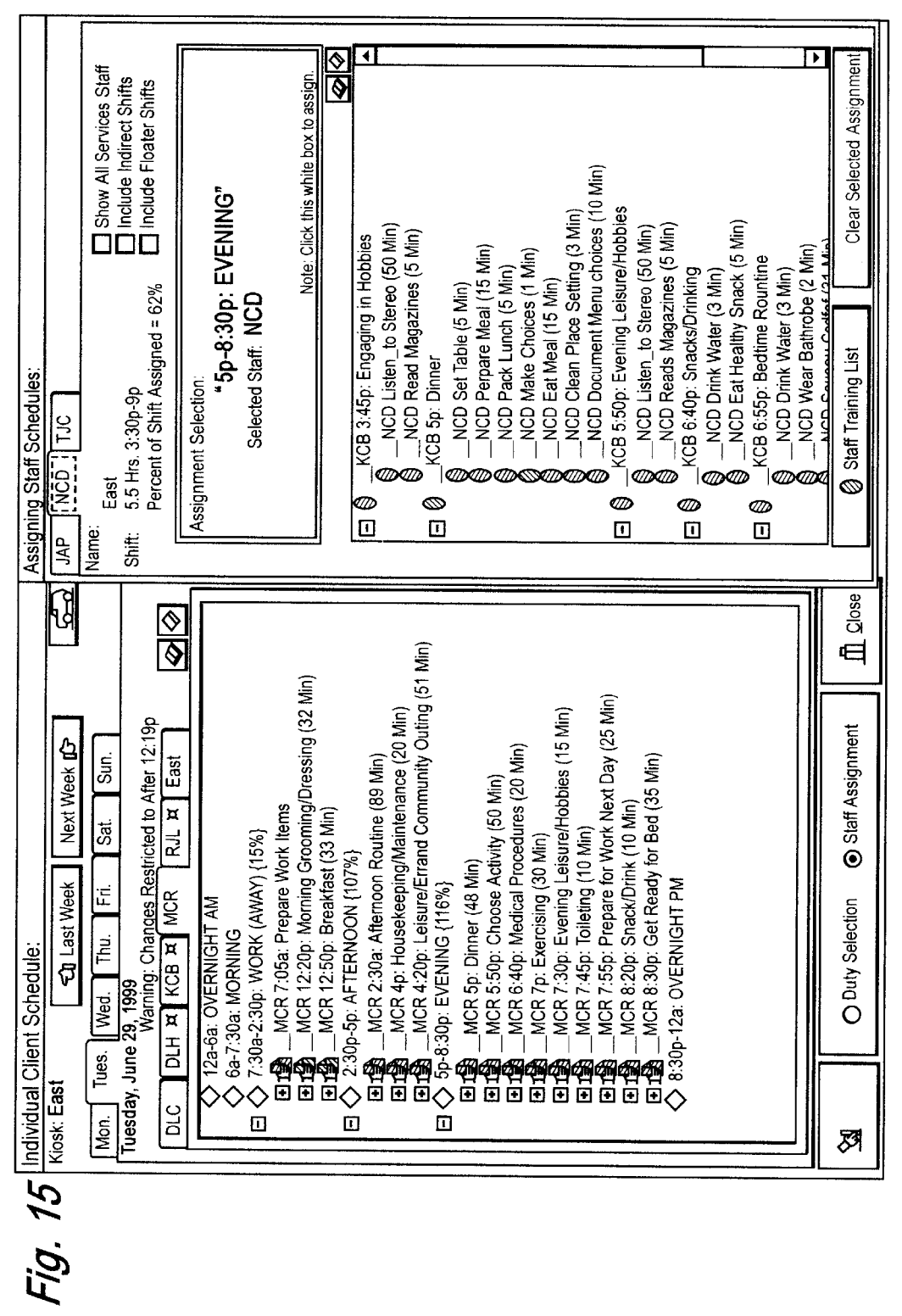

Using the planner process 122, supervisors assign duties for each client's daily schedule. Decisions on duties to be posted are made during the duty definition process. Each duty is assigned to specific days of the week and a time of day (morning, afternoon etc.). When posting, colored icons appear next to each duty to indicate if the frequency has been met for the day or week. This process ensures that duties meet minimum frequency requirements specified in the duty definition. An example of a screen showing the assignment of duties to staff is shown in FIG. 15. Generally, there are three phases to the assignment of activities in the planner process 122:

1. Activity Selection: Each client's Planned Activities and Supported Services are selected on a daily basis by supervisors. When posting a client's daily schedule, all duties assigned to that day appear on the Posting screen for selection. The duties are organized by activity. Adjustments can be made to fit special circumstances, as shown for example in FIG. 16. For example, a typical Tuesday schedule can be modified for a medical appointment or special outing. An example of an activity is "Get ready for bed." Duties under this activity may include Bathe Self, Brush Teeth, Floss Teeth, Set Alarm Clock. When posting the activity "Get ready for bed" the duties within it are also posted.

2. Time Selection: Activities are posted to a time block in a logical order of events. The time allotments determined in the duty definition automatically calculate the total time to complete an activity and give a percentage of time filled with activities for each time frame. The time blocks includes morning, work (away), afternoon, evening, and overnight.

3. Personnel Assignment: Activities are assigned to qualified staff scheduled for the applicable time. After posting activities for each client, supervisors assign a staff person who will be responsible for the activities. The Master Scheduler provides information to display staff working for that day. The Personnel Registry ensures that scheduled staff are qualified to perform scheduled activities.

Figure 18:
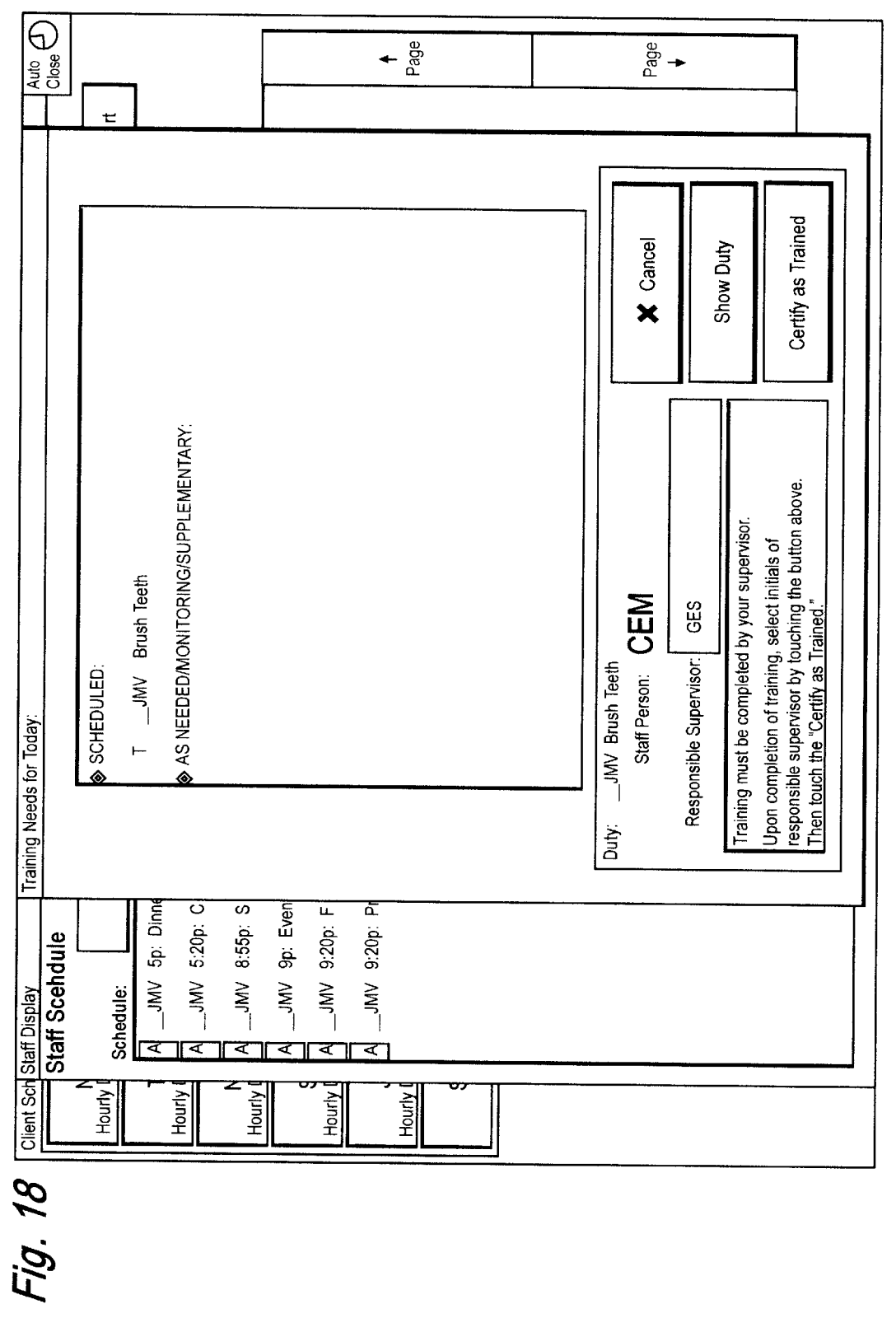

Other processes in the supervisory processes 120 include a process 134 to update training records which maintains a special training database 136 that contains all of the relevant training records (FIG. 17). A supervisor may indicate "Special Training" is required for a duty. When posting, supervisors are alerted of any staff requiring Special Training for scheduled duties. Training needs for each day can be viewed and printed for supervisor reference. Upon logging in for a shift, staff are alerted to any Special Training they need to obtain to complete their assigned duties, see FIG. 18. After training staff for a duty, the Program Training Record is updated. Generally, Special Training is required for all new and updated acquisition programs.

Figure 19:
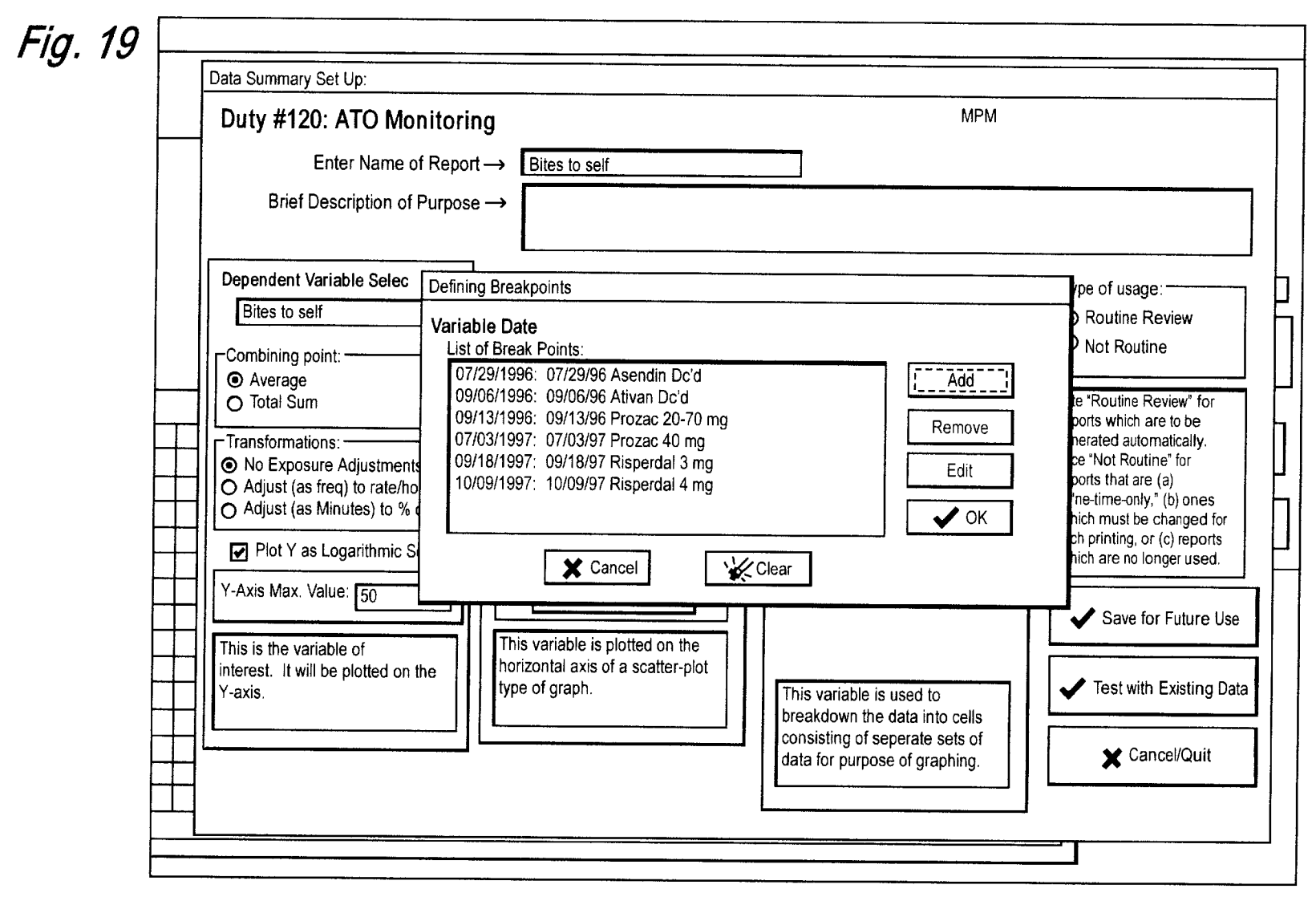

The supervisory processes 120 also include a variety of data review and analysis processes 138 which are used to interpret, assess, report and generate plans from a collection and analysis of the various information and data stored by the system. Because performance data associated with each activity is entered into the system 20 using standardized rating scales, it is possible for the analysis processes 138 to compile the performance data and generate one or more reports based on a meaningful analysis of the performance data. Standard statistical analysis and statistical software packages may also be used to create standardized or customized reports. The analysis processes can also compile periodic observations on health and behavior management issues of the clients and generate one or more reports based on an analysis of such periodic observations. An example of the special data setup to generate such a report on injurious behavior, for example, is shown in FIG. 19.

Objectives are established per program and progress is tracked from data collected at the kiosk. When an objective is met for a task, the program can be updated to teach an additional task within the duty. The client's participation in the duty may increase as the number of acquired tasks increase. For example, after a client learns how to apply shaving cream he is taught how to shave his face.

Referring again to FIG. 6, the display processes 140 are used to control the flow of collecting and displaying scheduling information and client performance and medical/historical data within the system 20. The daily duty process 142 interfaces with the personnel registry database 102, the client activity database 124 and the training records database 136 to create a daily work schedule for each staff member based on availability and qualifications of the staff members and appropriateness to the needs and preferences of the given client. The schedules are stored in the schedules database 144. The daily duty process 142 is a process which brings together all of the databases to create daily schedules for each client by selecting and ordering the appropriate activities into time-blocks (morning, afternoon, evening, etc.). Then, the daily duty process 142 is used to pair each of the duties corresponding to client activities with available and qualified staff members. When completed, such schedules are "posted" in the schedules database 144 so they can be transmitted to the direct-care staff in the living or working area of clients on the date and time indicated. Unlike the remaining display processes 140, the daily duty process 142 is typically only accessed by supervisory or management personnel.

The other major program in the display processes is the direct-care delivery process 146. This is the program that is used to collect performance data for client tasks in the task data database 148. Other data on health and historical conditions is tracked by the delivery process in the data log database 150. Such data flows back into the supervisory processes 120 with visual signals or alerts indicating where planning attention is needed to optimize the growth and maintenance of client skills.

There are two major subprograms for the direct-care delivery process 146, the interactive schedule display program 152 and the duty completion/data acquisition program 154. The interactive schedule display program 152 presents all the information needed for each staff member to complete the duties of their shift. Individual client schedules complete with recommended performance times and priorities can be examined. The same information is organized by individual staff member so that he or she may readily see the ordered list of activities and duties for which he or she is responsible.

The duty completion/data acquisition program 154 collects performance data for client tasks in the task data database 148 and a variety of other data in the data log database 150. The duty completion/data acquisition program 154 also interfaces with the special setup database 156 that establishes special setup parameters at a duty level or at a data acquisition level. Supervisors assign rating scales to each task step performed by a client. Three standardized scales rate performance, speed, and acceptance. The five point scales rate behavior relative to conventional expectations. Standard scales provide a consistent analysis of client behavior. Supervisors set criteria, or objectives, for each task. For example, a client's performance in washing laundry will maintain a '5' rating. After washing laundry direct-care staff rate client performance at the kiosk. This information is summarized in the planner process. A signal next to the duty "Wash Laundry" would indicate if program attention is needed. For example, last two opportunities the client rated below a '5'. Routine summaries updated and displayed on the planner database enable manageable data analysis and client assessment. An assessment of client performance is conducted at several levels. Speed and acceptance of a task can also be assessed. The planner process provides the supervisors with a signal if tasks within a duty have not met the defined criteria. The duties requiring program attention are then assessed in greater detail. Program efforts focus on teaching tasks, for example turning on a faucet may be taught within the duty of washing hands. Learning opportunities are planned by incorporating that task into other duties, such as brushing teeth or washing dishes, for example.

Preferably, both the interactive schedule display program 152 and the duty completion/data acquisition program 154 are interactive and direct-care staff actually confirm completion and enter the needed data in "real-time" as each duty is completed. The direct-care service process 146 can also issue "real-time" alerts for high-priority, time-sensitive duties such as medication delivery. Additionally, staff conveniences are incorporated into the direct-care service process 146 permitting the staff members to use internal "E-memo" communication, view work schedules of all staff, find key personnel assignments, setup vehicle usage schedules, see identification photographs, and search other information useful in their work environment.

Figure 20:
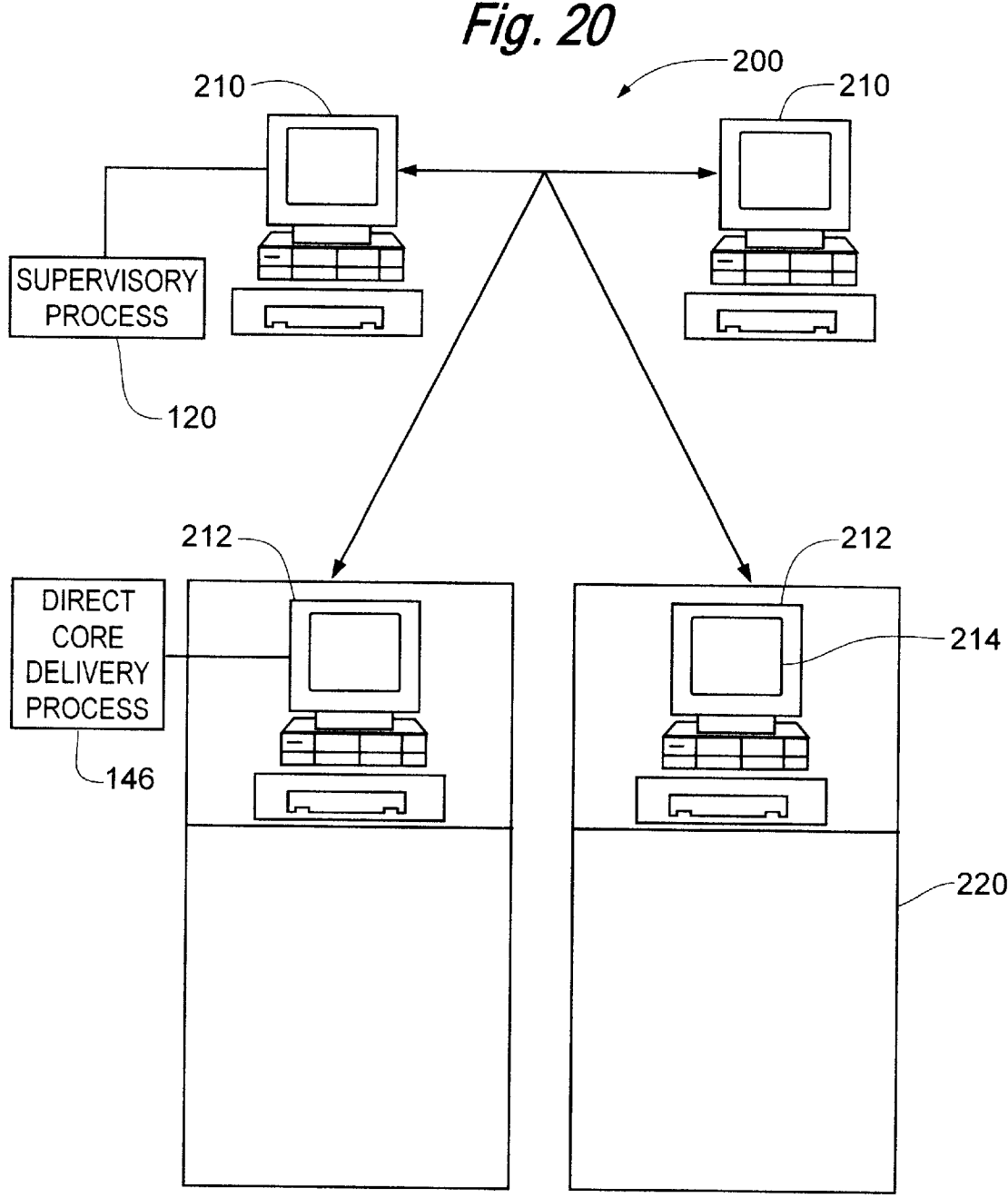
FIG. 20 is a schematic representation of the networked computer system on which the present invention is preferably implemented.

In the preferred embodiment of the SIM system 20 as shown in FIG. 20, a networked computer system 200 includes at least two computers 210, 212. Computer 210 is generally utilized as a supervisory computer performing the supervisory processes 120 as described in connection with FIG. 6. One or more computers 212 generally execute the direct-care delivery process 146 and are preferably implemented on computers which reside in the client living (or working) area. Although the preferred embodiment utilizes a networked computer system, it will be recognized that in smaller facilities, it may be more attractive to implement all of the functions on a single computer system in which access to certain of the processes is protected by passwords or similar authentication processes. In the preferred embodiment of the present invention, the computer processes implemented on the computers 212 are designed to use "fingertip" activation on a touch-screen 214. While the touch-screen is not essential as the program can work equally well with a "mouse" or keyboard input, it has been found that the touch-screen 214 in a stand-up configuration such as the kiosk enclosures 220 makes it more efficient for staff who cannot readily sit down to use a computer.

For certain types of clients, kiosk enclosures 220 as shown in FIG. 20 are used to protect the physical and/or access integrity of the SIM system 20. The kiosk enclosures 220 may be used because some clients are unaware that the computer is fragile, or to limit physical access in a manner that augments the security of the system 20 in addition to the preferred sign-in system for enabling access to the system. The kiosk enclosures 220 are preferably fabricated using fine wood and intended to be minimally intrusive in the clients' environment while readily available for use by direct-care staff.

Figure 21:
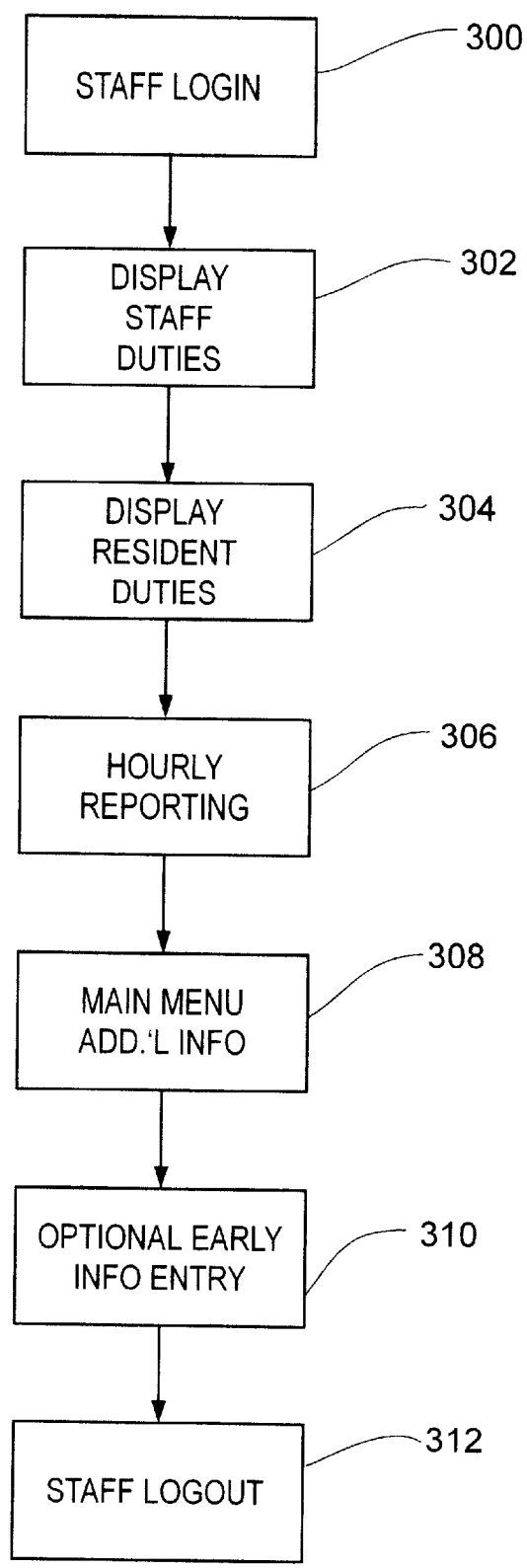
FIG. 21 is a flow chart of the overall flow of staff member operation of the present invention.

The operational flow of the preferred embodiment of the SIM system 20 in accordance with the present invention will now be described. Referring now to FIG. 21, the operational flow and screen display, respectively are shown for the initial interface of a staff member with the direct-care services process 146 will be described. At step 300, the staff member logs in by accessing the log in process. Staff members always log in under only their own initials. If a staff member cannot find his or her initials, they are instructed to select the "show all scheduled staff" on the log in screen. If they still cannot find their initials, they must use the "look up" option, where the staff member is asked to select his or her department, position, and times that you will be working. After these selections have been made, the staff member's name will appear on the initial log in screen.

Figure 22:
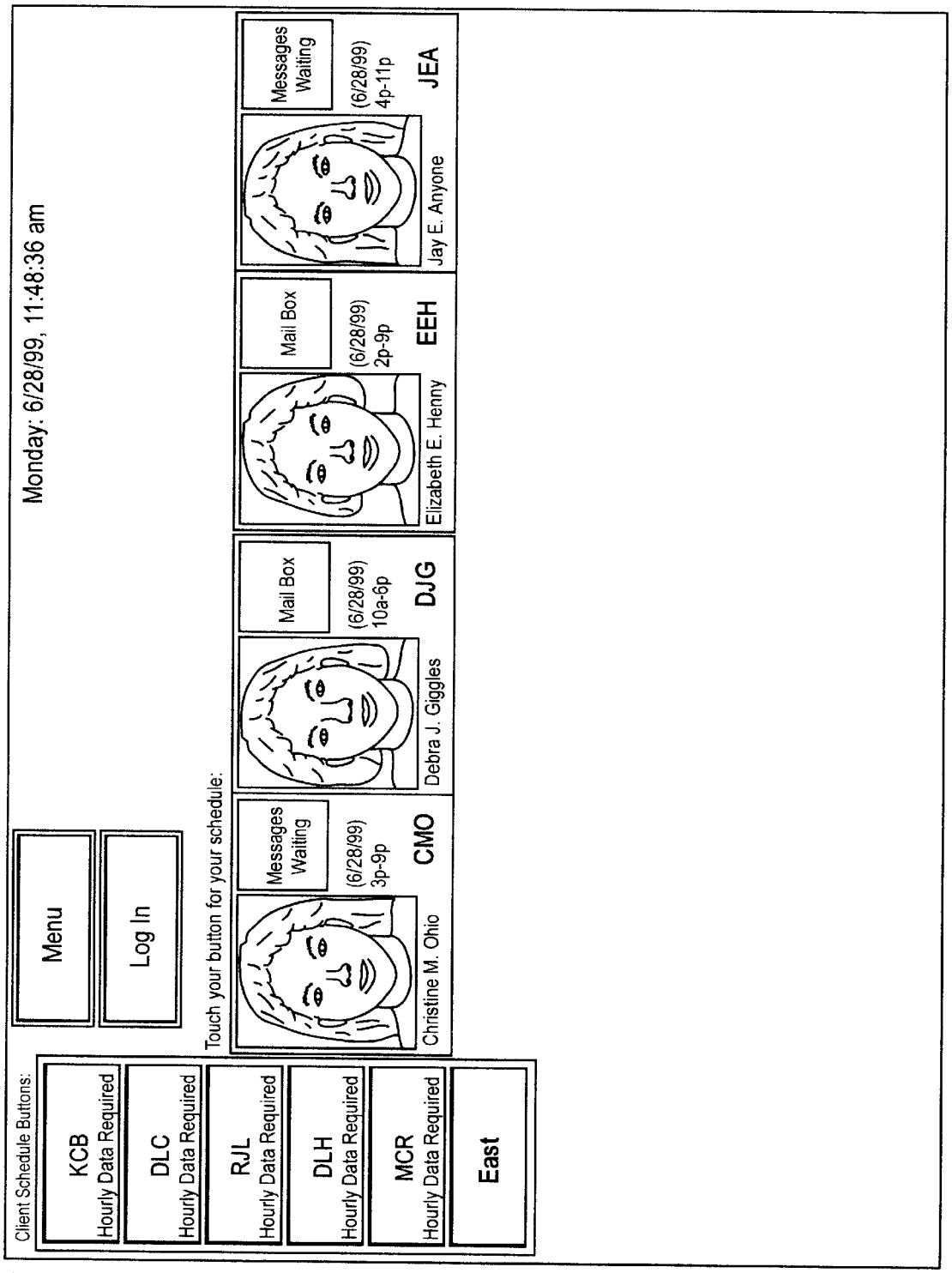

At step 302, the duties of a staff member are displayed. Upon logging in, a button will appear on the screen shown in FIG. 22 with the staff member's photograph and initials on it. If this button is touched, a screen will appear with list of activities assigned to the particular staff member for completion will be displayed on the left side of the screen, as shown in FIG. 23. While the staff member is looking at his or her list of activities they may touch a specific activity to expand it displaying the duties that fall within. Upon touching the duty a separate screen will appear displaying two screens which may be viewed by using tabs at the bottom. One screen displays the task steps to follow for duty completion, while the "Special Notes" option displays the supplementary text as set up in the duty definition, see FIG. 24. The duty screen also allows several other operations including:

1. Duty reassignment—if this option is chosen, a display will appear allowing reassignment to a different staff person. When attempting to reassign a duty to a staff person who has not met the training requirements, a message will appear as an alert that the training will need to be completed if the duty is assigned to that person.
2. Print—this option may be used to print a hard copy of the task steps with space for data entry (FIG. 25).
3. Enter data—when selected this option leads the user through the data entry process asking for ratings on the standard rating scales, or special data as specified in the duty definition. Upon entering data the duty will disappear from the staff screen.

Figure 26:
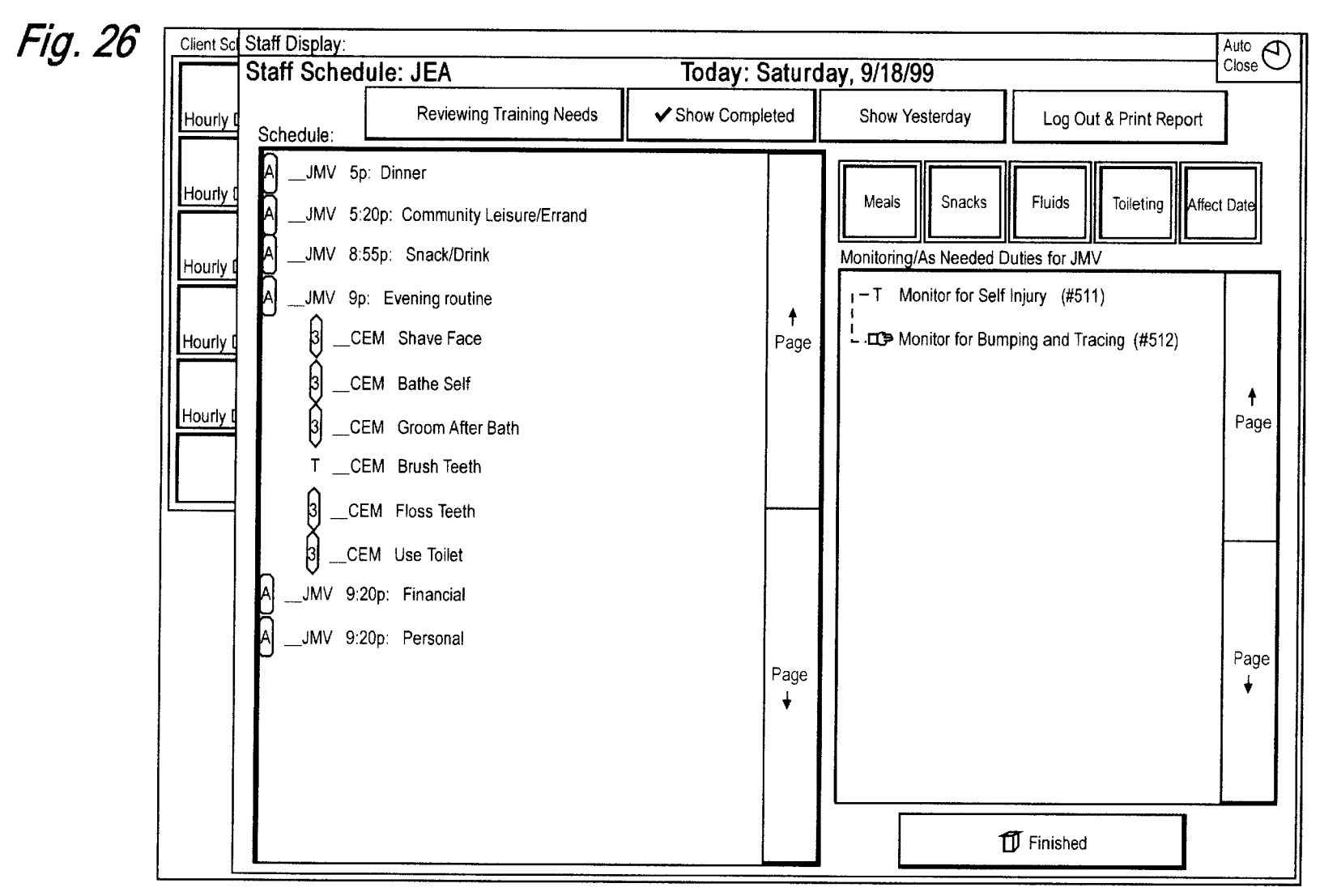

As duties or activities are touched for a particular client, the screen on the right side will list the monitoring and as needed duties for the indicated person as well as several buttons allowing for entry of health information (see FIG. 26). These duties when touched, will provide the staff person with the same information and options as listed above. The colored buttons labeled "Meals", "Toileting", "Snacks", and "Fluids" should be accessed when any of these events occur in order to enter basic health tracking information.

Along with the health buttons, once an hour, an additional button will appear that is labeled "Affect entry". When this button is visible, staff are instructed to touch it in order to make an hourly entry which best describes the client's general affect or disposition. This information is typically entered every hour on the hour in step 306, but is made available for early entry under certain circumstances at step 310.

At step 312, a staff member can log out of the system. When a staff member goes to log out, the screen will alert the staff member if they have uncompleted duties for the shift they are logged in for. Some duties may be important to reassign, others may be left as uncompleted. Any uncompleted duties will appear on the sign out sheet, along with space to write in an explanation, see FIG. 27.

Figure 28:
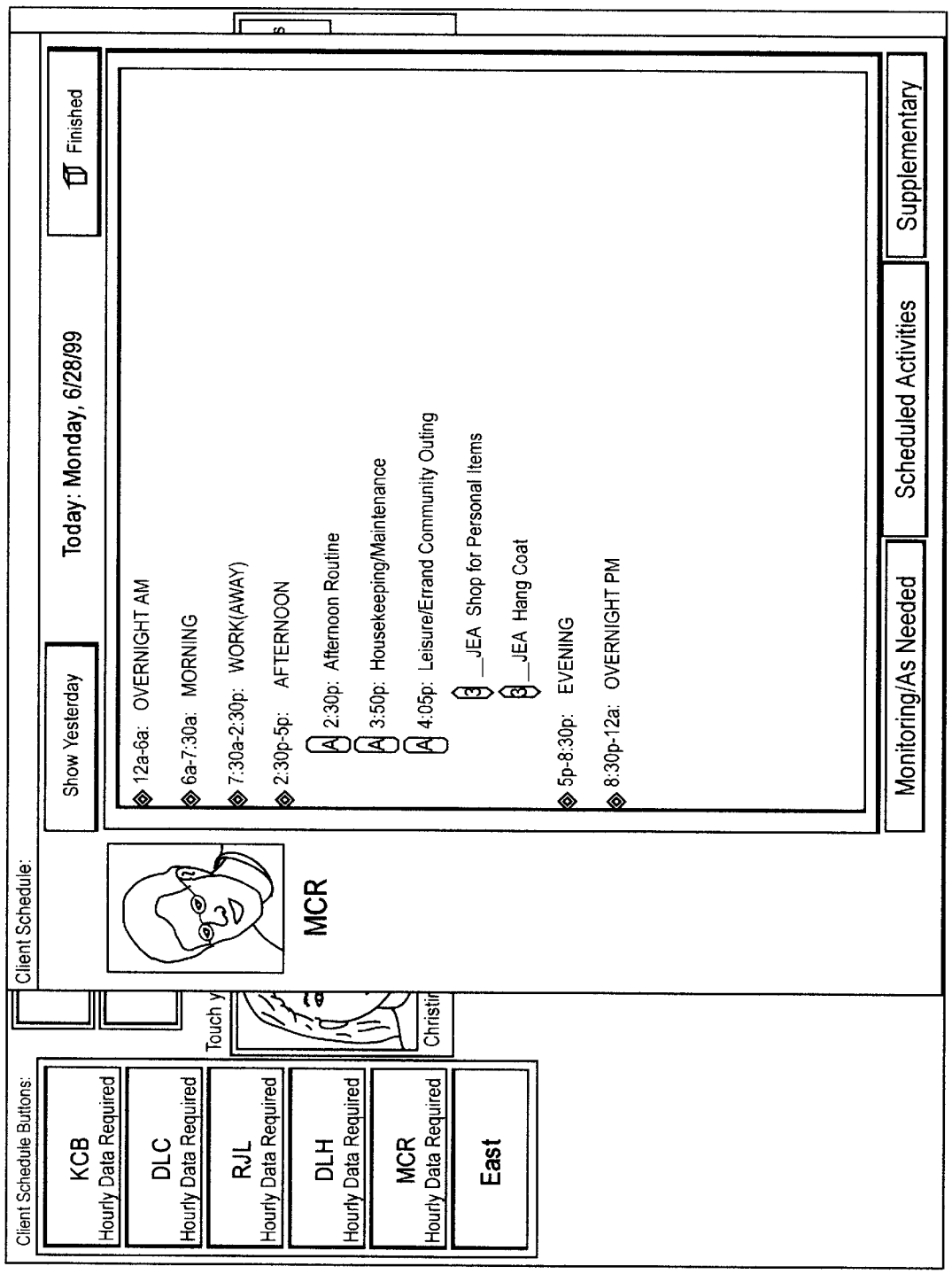

At step 304, the duties or activities of the various clients may be displayed. On the left side of the main screen (shown in FIG. 22), there will be buttons with client initials. If any of these buttons are touched, a display will appear for that client which actually contains three screens, as shown in FIG. 28, each of which can be accessed using the tabs below. The three screens will display the following categories of duties:

1. Monitoring/as needed—This screen will display those duties which cannot be scheduled at a specific time. For example, many behavioral interventions are only performed when challenging behaviors occur, and therefore cannot be scheduled.
2. Day's Schedule—This screen lists all the activities and duties which have been scheduled for the day. The duties, when touched, offer all the same operations that can be performed from the staff screen. When duties are completed, they will not disappear but will appear with a check-mark.
3. Supplementary—This screen will display duties which can be completed as supplements to the regular day's schedule. When touched, these duties offer the standard operations In a column on the left of the client screen are the same health and affect buttons which appear on the staff screen. These buttons function the same as when accessed from the staff screen in order to document health related events for a given client as they occur.

To alert staff of mandatory duties (those which must be completed at the specific time), the button faces of the corresponding staff person and client will turn red as an alert to access these screens, review information, and complete the duty in a timely fashion.

Figure 29:
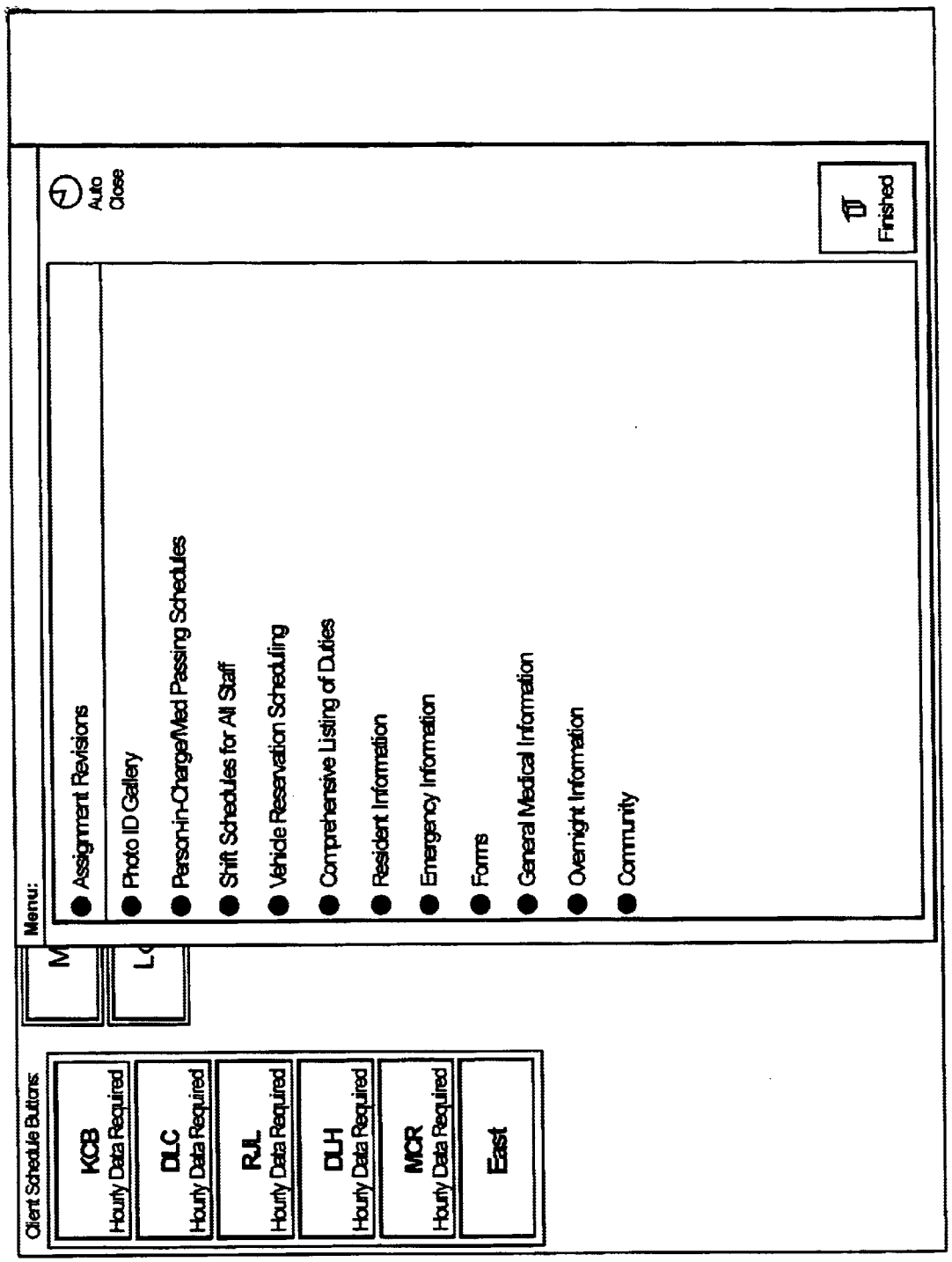

At step 308, a staff member can access the main menu button in the upper left corner to view basic information or perform addition operations as shown in FIG. 29. The details of each of these additional operations are as follows:

1. Assignment Revisions—This screen will help to reassign several duties at once as in the case of staff illness. Both staff members involved in the duty reassignment must first be selected, then the duties can be moved from one to another using the specified buttons. This option is especially useful in the event of staff illness.
2. Photo ID Gallery—This option contains photographs of all persons listed in the registry, including: clients, staff members, family members, consultants, etc.
3. PIC/Med Passing—This screen will display who is assigned to pass medications and who is assigned PIC duties for that day. As in staff work schedules, it is possible to scroll back or forward a day.
4. Shift Schedules for all Staff—A staff member may view work schedules for everyone working in each department for that day. It is also possible to move back or forward one day.
5. Reprint Daily Work Reports—Any daily report which has not yet been turned in, reviewed, and "confirmed" by a supervisor may be reprinted the kiosk using this process.
6. Vehicle Reservation Scheduling—At the kiosk, staff can view vehicle availability and reserve time slots for vehicle use. At the poster, supervisors can reserve a vehicle when posting activities for the day. These reservations may be a on a "one time only" basis or routinely scheduled.
7. Comprehensive Listing of all Duties—This process allows you to review all active duties for a particular resident from the kiosk. This function is for viewing purposes only and does not allow for data entry or reassignment of a duty.
8. Client Information—By accessing this option, a staff member may review general text information regarding clients. It is intended to be general information which is especially useful during training but also good for quick reference. Topics included are family background, likes and dislikes, special concerns, medical information, communication issues, and prompting methods.
9. Forms—From this screen, a staff member may review and print miscellaneous forms.
10. General Medical Information—This is where general medical information is accessed, such as med error procedures. Specific medical information will appear under client information.
11. Overnight Information—This option provides quick access to information regarding general overnight information. Specific information regarding individual clients is listed under client information.
12. Emergency Information—This allows the staff member to quickly access any information regarding emergency procedures.

Many screens are designed to disappear after a certain amount of time has passed, and no functions have been performed. Timers in the upper right corner will alert the users as to how much time is left before it disappears. If more time is desired, touching anywhere on the screen will reset the timer. Before a screen actually disappears, there will be a series of beeps as warning. This is done to limit the number of functions going on at the same so that the system does not get overloaded.

The SIM system 20 is designed to allow for quick and convenient communication between all staff members via the internal memo database 116 and internal messaging module 114. When there is a message waiting for the staff, it is indicated by a flag on their button indicating that a message is waiting. After reading a message, the staff member should touch, "Mark as Delivered" to indicate that the message has been received and read. It will be noted that unlike conventional e-mail systems that address messages to specific computer destinations in a networked computer system, the messaging module 114 provides a general notice in the kiost station computers 212 that staff messages exist and then the staff members must determine which message, based on initial ID, is intended for them.

What is claimed is:

1. A method of providing a standardized information management system for use in a long-term residence facility, the method comprising:

creating in a computer database:

a set of defined duties for each of a plurality of clients residing at the long-term residence facility who have a reduced capacity to perform normal daily living activities, each duty representing a unit of assignable work selected from a set of a daily living activity or a developmental opportunity that involves a client, at least one staff member of the long-term residence facility who provides life care services designed to support and maintain normal daily living activities and developmental opportunities for each of the plurality of clients for extended periods of time, or both;

a set of defined activities suitable for each of the plurality of clients, each activity representing a selective clustering of one or more defined duties; and a comprehensive daily plan for each of the plurality of clients, each daily plan representing a schedule of activities selected from the relevant set of activities defined for a given client that are assigned as responsibilities for selected staff members based on availability and qualifications of the staff members and appropriateness to the needs and preferences of the given client; and using a computer system having access to the computer database to:

display the daily plans to the staff members;

enter performance data associated with each activity for each of the plurality of clients using standardized rating scales; and compile the performance data and generate one or more reports based on an analysis of the performance data.

2. The method of claim 1 wherein the computer system is further used to:

record periodic observations on health and/or behavior management issues of the plurality of clients; and compile the periodic observations and generate one or more reports based on an analysis of the periodic observations.

3. The method of claim 1 wherein the set of defined duties is created by assembling a series of tasks that comprise a given duty, each task being individually definable using a standardized database process that structures the definition of each task within certain parameters and provides a reusable set of resources once the tasks are created in the database.

4. The method of claim 1 wherein the computer database further comprises a set of comprehensive historical and reference information about each of the plurality of clients created in the computer database and wherein the computer system is used to access the computer database to display the set historical and reference information for a selected client to the staff members.

5. The method of claim 1 wherein the performance data is optionally entered using the computer system and a specialized data collection set-up process in place of the standardized rating scales.

6. A standardized information management system for use in a long-term residence facility, the system comprising:

a computer system executing at least three software processes, including:

a supervisory process means for planning service needs and creating daily schedules for each of a plurality of clients residing at the long-term residence facility, who have a reduced capacity to perform normal daily living activities, a comprehensive daily plan that is stored in a database in the computer system, with each daily plan representing a schedule of activities selected from a relevant set of activities representing at least daily living activities defined for a given client;

a utility process means for managing personnel records and work shift schedules of a plurality of staff members of the long-term residence facility, who provide life care services designed to support and maintain normal daily living activities for each of the plurality of clients for extended periods of time, and are assigning selected activities of each daily plan as responsibilities for selected staff members based on availability and qualifications of the staff members and appropriateness to the needs and preferences of the given client as stored in a database in the computer system; and a display process means for displaying current work information to staff members based on the work shift schedules created by the utility process mean and for entering performance data by staff members about client performance of activities scheduled for the daily plan into a database in the computer system using standardized rating scales.

7. The standardized information management system of claim 6 further comprising:

means for compiling the performance data and generating one or more reports based on an analysis of the performance data.

8. The standardized information management system of claim 6 wherein the display process means further includes means for recording by staff members periodic observations on health and/or behavior management issues of each of the plurality of clients, and wherein the information management system further comprises means for compiling the periodic observations and generating one or more reports based on an analysis of the periodic observations.

9. The standardized information management system of claim 6 wherein the computer system comprises a networked computer system including at least two separate computers.

10. The standardized information management system of claim 9 wherein at least one of the computers includes a kiosk display station located in an easily accessible area of the long-term residence facility such that staff members can display current work information and enter performance data on clients using the kiosk display station.

11. The standardized information management system of claim 10 wherein the kiosk display station includes a touch screen display protected from access by the clients to prevent damage or inappropriate access.

12. The standardized information management system of claim 6 wherein the supervisory process means further comprises:

a database accessible by the computer system that stores a set of defined duties for each of a plurality of clients, each duty representing a unit of assignable work that involves a client, a staff member or both; and means for selective clustering of one or more defined duties into an activity to be scheduled by the supervisory process means.

13. The standardized information management system of claim 12 further comprising:

means for assembling a series of tasks to define a given duty, each task being individually definable using a standardized database process that structures the definition of each task within certain parameters and provides a reusable set of resources once the tasks are created in the database process.

14. The standardized information management system of claim 6 wherein the display process means optionally utilizes a specialized data collection set-up process in place of the standardized rating scales to collect the performance data.

15. A standardized method for creating and displaying tasks to be performed at a long-term residence facility, the standardized method comprising:

identifying a task to be defined for a client residing at the long-term residence facility, who has a reduced capacity to perform normal daily living activities, the task being selected from a set of normal daily living activities or developmental opportunities appropriate for that client;

defining a condition for when the task is to be performed;

defining an action for the task;

defining an object of the action for the task;

storing the condition, the action and the object for the task in a computer database as one of a set of tasks defined for the client;

repeating previous steps to make a plurality of different tasks individualized to different clients; and using a computer system to access the computer database and selectively display one or more tasks for one or more of a plurality of clients to a staff member of the long term residence facility, who provides life care services designed to support and maintain normal daily living activities and developmental opportunities for each of the plurality of clients for extended periods of time, in a standardized format.

16. The standardized method of claim 15 further comprising:

defining a tool to be used for the action; and storing the tool as part of the task in the computer database.

17. The standardized method of claim 15 further comprising:

defining a criterion for terms under which the action is to be performed; and storing the criterion as part of the task in the computer database.

18. The standardized method of claim 15 wherein a set of tasks are assembled as step-by-step processes to define a duty, a duty being a unit of assignable work that involves a client, a staff member or both.

19. The standardized method of claim 18 wherein duties are selectively clustered together to form activities and wherein the activities are then scheduled as staff responsibilities based on staff availability and qualifications and appropriateness to client needs and preferences.

20. The standardized method of claim 19 wherein a comprehensive plan for each client is created by scheduling relevant activities for that client on a daily basis.

21. The standardized method of claim 15 wherein the tasks to be performed are dynamically adaptable for each client over an extended period of care to provide an individualized care protocol for that client.

22. A method of providing a standardized reporting of health and behavioral issues for use in a long-term residence facility, the method comprising:

creating in a computer database:

a set of defined activities suitable for each of a plurality of clients of the long-term residence facility having limited capacity for communication, each activity representing a normal daily living activity or developmental opportunity appropriate for that client;

a comprehensive daily plan for each of the plurality of clients, each daily plan representing a schedule of activities selected from the relevant set of activities defined for a given client; and a record of medications provided to each of the plurality of clients; and using a computer system operated by a plurality of staff members of the long-term residence facility, who provide life care services designed to support and maintain normal daily living activities and developmental opportunities for each of the plurality of clients for extended periods of time, and having access to the computer database to:

display the daily plans to the staff members;

enter performance data associated with each activity for each of the plurality of clients using standardized rating scales;

enter periodic observations on health and/or behavior management issues of each of the plurality of clients; and compile the performance data and generate one or more reports based on a longitudinal analysis of the performance data and periodic observations as a function of changes in the medications for each of the plurality of clients.

* * * * *